United States Patent
Arnone et al.

(10) Patent No.: US 7,174,037 B2
(45) Date of Patent: Feb. 6, 2007

(54) IMAGING APPARATUS AND METHOD

(75) Inventors: Donald Dominic Arnone, Cambridge (GB); Craig Michael Ciesla, Cambridge (GB); Bryan Edward Cole, Cambridge (GB)

(73) Assignee: Teraview Limited (GB)

( * ) Notice: Subject to any disclaimer, the term of this patent is extended or adjusted under 35 U.S.C. 154(b) by 419 days.

(21) Appl. No.: 10/220,479

(22) PCT Filed: Feb. 28, 2001

(86) PCT No.: PCT/GB01/00860

§ 371 (c)(1), (2), (4) Date: Mar. 24, 2003

(87) PCT Pub. No.: WO01/65239

PCT Pub. Date: Sep. 7, 2001

(65) Prior Publication Data

US 2003/0178584 A1   Sep. 25, 2003

(30) Foreign Application Priority Data

Feb. 28, 2000 (GB) ............................. 0004668.0

(51) Int. Cl.
*G06K 9/00* (2006.01)

(52) U.S. Cl. ............... 382/128; 250/341.1; 250/341.8; 250/495.1

(58) Field of Classification Search ........ 382/128–134; 378/4, 21, 23–27, 140, 185, 901; 600/310, 600/407, 425, 436, 473, 476; 250/253, 302, 250/324, 341.1, 341.8, 495.1; 324/637–639

See application file for complete search history.

(56) References Cited

U.S. PATENT DOCUMENTS

| 4,533,829 | A | * | 8/1985 | Miceli et al. | .......... 250/227.27 |
| 5,293,213 | A | | 3/1994 | Mastromarino et al. | |
| 5,360,973 | A | * | 11/1994 | Webb | .................... 250/370.01 |
| 5,590,168 | A | * | 12/1996 | Iketaki | ....................... 378/43 |
| 5,710,430 | A | * | 1/1998 | Nuss | ...................... 250/358.1 |

(Continued)

FOREIGN PATENT DOCUMENTS

EP   0 828 143 A2   3/1998

(Continued)

OTHER PUBLICATIONS

D.M. Mittleman, et al., "T-Ray Imaging", *IEEE Journal of Selected Topics In Quantum Electronics*, U.S., IEEE Service Center, vol. 2, No. 3, Sep. 1, 1996, pp. 679-692.

(Continued)

*Primary Examiner*—Jingge Wu
*Assistant Examiner*—Abolfazl Tabatabai
(74) *Attorney, Agent, or Firm*—Ostrolenk, Faber, Gerb & Soffen, LLP

(57) ABSTRACT

An apparatus and method for imaging a sample, the apparatus including a source for irradiating a sample with a beam of substantially continuous electromagnetic radiation having a frequency in the range 25 GHz to 100 THz; means for subdividing an area of the sample which is to be imaged into a two dimensional array of pixels; means for detecting radiation from each pixel wherein the detector is configured to detect a phase dependent quantity of the detected radiation which is measured relative to the radiation which irradiates the sample.

24 Claims, 23 Drawing Sheets

U.S. PATENT DOCUMENTS 5,813,987 A * 9/1998 Modell et al. .............. 600/473
5,886,534 A * 3/1999 Bakhtiari et al. ........... 324/642
6,026,173 A * 2/2000 Svenson et al. ............ 382/131

FOREIGN PATENT DOCUMENTS

| EP | 0 828 162 A2 | 3/1998 |
|---|---|---|
| EP | 0828143 | 3/1998 |
| EP | 0828162 | 3/1998 |
| EP | 0841548 | 5/1998 |
| EP | 0 864 857 A1 | 9/1998 |
| WO | 00/50859 | 8/2000 |

OTHER PUBLICATIONS

Q. Wu, et al., "Two-Dimensional Electro-Optic Imaging of THz Beams", *Applied Physics Letters*, U.S., American Institute of Physics, New York, vol. 69, No. 8, Aug. 19, 1996, pp. 1026-1028.

* cited by examiner

Fig. 7 *An actual device may have this triple well unit repeated 20 or 30 times, yielding a device with many layers. Device will be placed in fabry perot resonator.

Fig. 8(a) Vertical Transition

Fig. 8(b) Vertical Transition + LO-phonon emission

Fig. 8(c) Diagonal Transition

IMAGING APPARATUS AND METHOD

BACK GROUND OF THE INVENTION

1. Field of the Invention

The present invention relates to the field of imaging apparatus and methods. More specifically, the present invention relates to imaging using frequencies in the range overlapping the infrared and microwave parts of the spectrum. This frequency range encompasses the so-called Terahertz (THz) frequency range and is often referred to as Terahertz radiation.

2. Description of Related Art

Recently, there has been considerable interest in THz pulse imaging (TPI) which is showing promising results for both medical and non-medical use. THz radiation is non ionising radiation. Therefore, it is believed to be medically safer than well established x-ray techniques. The lower power levels used (nW to µW) also suggest that heating effects are not problematic, as may be the case with microwaves for example.

THz pulse imaging uses a plurality of frequencies within a single pulse in order to probe the frequency dependent absorption characteristics of the sample under test. Pulsed sources suffer from the drawback that they are expensive and also it is difficult to efficiently transmit pulses down optical waveguides etc. The complexity of the transmitted and reflected pulses, in lossless and in particular lossy mediums, also renders interpretation of the pulsed data difficult.

BRIEF SUMMARY OF THE INVENTION

The present invention addresses the above problems and, in a first aspect, provides an apparatus for imaging a sample, the apparatus comprising:
- a source for irradiating a sample with a beam of substantially continuous electromagnetic radiation having a frequency in the range from 25 GHz to 100 THz;
- means for subdividing an area of the sample which is to be imaged into a two dimensional array of pixels,
- means for detecting radiation from each pixel wherein the detector is configured to detect a phase dependent quantity of the detected radiation which is measured relative to the radiation which irradiates the sample.

The term substantially continuous is hereinafter taken to mean that the radiation source outputs radiation for all or most of the time, if the output of or from the source is gated such that the flow of radiation from the source is periodically interrupted, the length of the interruptions will be shorter than the length of time over which the source is continuously producing radiation.

A single or plurality of frequencies in the range from 25 GHz to 100 THz is used. Preferably, the frequency is in the range from 50 GHz to 84 THz, more preferably 100 GHz to 20 THz.

The present invention uses a single frequency or a plurality of discrete frequencies through the sample at any one time. Information concerning the internal structure of the sample can be determined from radiation of a single frequency as variations in the phase of the radiation as it passes through the sample will allow structural information such as the width of the sample and compositional information about the sample to be obtained.

The use of just a single frequency through the sample at any one time means that relatively inexpensive single frequency dedicated sources may be used.

The frequency of the radiation incident on the sample can be varied by known methods in order to obtain information about the frequency dependent characteristics of the sample.

Alternatively, the radiation incident on the sample can comprise two or more discrete frequencies. These frequencies are preferably selected to probe different materials or components in the sample.

The detector is preferably configured to detect a phase dependent quantity of each frequency component relative to the radiation which irradiates the sample.

This means that broadband incoherent or short coherence length radiation may also be used as random variations in the phase between the different frequency components do not matter since the phrase change for each frequency component is measured.

It is difficult to produce an efficient and powerful source for THz radiation as there is no good naturally occurring source of such radiation. Previously, there have been two main methods for generating THz radiation. The first has been to use a solid state radiation source such as a Gunn diode, molecular laser, free electron laser, cascade laser etc. The second has been to convert commonly available radiation such a radiation in the visible or near IR range, lower frequency microwaves into THz regime using a frequency conversion member.

The frequency conversion member could be an optically non-linear material which is configured to emit a beam of emitted radiation in response to irradiation by two input beams, or a photoconductive antenna which upon application of an electric field is configured to emit a beam of emitted radiation in response to irradiation by two input beams. The emitted beam has a frequency which is equal to the difference of the two input beams. In these examples, the input beams will generally have a frequency which is in the visible or near IR frequency range.

Preferably, two beams of input radiation will be supplied by two continuous wave (CW) sources. Such continuous wave sources may be two near-infrared/visible lasers. Three or more continuous wave sources may also be used to generate an emitted beam having two or more frequencies. Alternatively, a single source running in multi mode, i.e. outputting two or more wavelengths at the same time, could also be used. A broadband source could also be used.

Alternatively, the optically non-linear member could be configured to emit a beam of emitted radiation in response to irradiation by an input beam, the emitted radiation having a frequency which is a harmonic of the frequency of the input radiation. The input beam could have a frequency in the low frequency microwave range.

The detector measures a change in phase dependent quantity of the radiation, this might be a direct measurement of the phase itself, or a measurement of the electric field which is transmitted through or reflected from the sample, the amplitude of which will be phase dependent etc.

In order for the detector to be able to detect the phase dependent quantity with respect to the radiation which irradiates the sample, the detector needs to have some way of knowing information about the phase of the radiation which irradiates the sample. A convenient way to achieve this is for the detector to receive a probe beam which has a phase related to that of the radiation which is used to irradiate the sample.

The probe beam could be obtained by splitting the one or more of the input beams or it could be provided by splitting the Terahertz beam used to irradiate the sample. The detector could directly detect the probe beam or the probe beam could be combined with the radiation which has been transmitted through or reflected from the sample before detection. This combining of the two beams could be achieved by using a mixing component.

As previously mentioned, broadband incoherent radiation could also be used. A broadband source generates radiation having a plurality of different frequencies. Unlike pulsed laser sources, phase relationship between the different frequency components. Thus, there is a random phase relationship between the different frequency components in a broadband source. If part of this broadband beam is also used as the probe beam then the fact that the beam is incoherent is of no consequence, since only the phase difference for each frequency component is measured.

In order to detect the phase dependent quantity, the apparatus further preferably comprises a phase control means, which can be used to control the phase of the probe beam or the beam of radiation which irradiates the sample. The phase control means may be provided by an optical delay line which varies the length of the path of the probe beam with respect to the length of the path of the irradiating radiation. Of course, the length of the path of the irradiating radiation could be varied with respect to the length of the path of the probe beam to achieve the same result.

The length of the path of the probe beam can be varied during the imaging process to obtain information relating to the phase of the detected radiation. The path length of the probe beam could also be oscillated or dithered about a point. The oscillation period or 'dithering' period could be used for lock-in detection by the detector.

Once the THz is emitted from the sample, detection is required. A particularly useful detection technique is to use Electro-Optic Sampling (EOS) which uses the AC Pockels effect. The detector may comprise a photoconductive antenna.

It is also possible to combine the beam which has been reflected from or transmitted by the sample with another beam of radiation which has substantially the same wavelength or which differs in frequency by at most 10 GHz. Such combined radiation can be detected using a bolometer, Schottky diode etc.

Possible materials which posses good non linear characteristics for any of the above mechanisms are GaAs or Si based semiconductors. More preferably, a crystalline structure is used. The following are further examples of possible materials:

$NH_4H_2PO_4$, ADP, $KH_2PO_4$, $KH_2ASO_4$, Quartz, $AlPO_4$, ZnO, CdS, GaP, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_3$, ZnS, organic crystals such as DAST (4-N-methylstilbazolium).

The apparatus is used to image an area of the sample. An area of the sample can be imaged in a number of different ways. For example, the sample can be moved with respect to the beam or the beam with respect to the sample. Alternatively, the sample could be illuminated with a wide beam or a plurality of beams from different sources. The detector could also be configured in a similar manner. The detector could comprises a CCD camera which will allow a large area of the sample to be examined at once.

The above description has been mainly concerned with generating and detecting THz radiation using non-linear materials. However, there are other methods. A particularly useful detection method is to combine the THz radiation which is emitted from the sample with another beam of THz radiation. This radiation can then be passed through a non-linear member which allows the difference of the radiation, which may typically be in the GHz range to be detected. 1 GHz is in the microwave range and detectors for such radiation are well known in the art.

The present invention can use a small number of single frequency sources in order to generate the THz radiation. Therefore, it is possible to construct a highly efficient THz probe where the probe is located remote from the source of input radiation. For example, if the source of input radiation is two visible wavelength CW lasers, two fibre optic cables which are each optimised to the frequency of the relevant CW laser can be used to carry the input radiation to a probe. The probe may be for example an endoscope which can be inserted into the human body or a surface probe for skin or teeth, or other non-medical items. The purpose of the probe may be either to collect local spectral or other diagnostic information, or alternatively it may be run in an imaging mode by being dragged across the surface or having the surface dragged across it. The THz radiation can then be generated within the endoscope by using a frequency conversion member The THz radiation can then be detected in the same manner as previously described. The probe or reference beam can be split from one of the CW laser inputs. The reference beam with a rotated polarisation can then be transmitted down a polarisation preserving optical fibre back to analysis equipment. Alternatively, photoconductive emitters and detectors may be placed on the end of the fibre, in which case electrical power may have to be supplied by additional wires.

A broadband source may also be used to provide the radiation. It is difficult to send a plurality of frequencies down a fibre as a pulse since the high peak power of the pulse can given rise to non-linear effects what may destroy the pulse. Broadband radiation provides a continuous lower level and hence does not suffer from this problem. Also, a single multimode CW source may also be used.

In a second aspect, the present invention provides a method of imaging a sample, the method comprising the steps of irradiating a sample with substantially continuous radiation with a frequency in the range form 25 GHz to 100 THz; subdividing an area of the sample which is to be imaged into a two dimensional array of pixels; detecting radiation from each pixel, wherein the detector is configured to detect a phase dependent quantity of the detected radiation which is measured relative to the radiation which irradiates the sample.

In a third aspect, the present invention provides an apparatus for investigating a sample, the apparatus comprising means for generating a beam of substantially continuous electromagnetic source radiation having a frequency in the range 25 GHz to 100 THz; means for moving the sample relative to the beam to scan the beam over the sample; means for detecting the radiation transmitted by or reflected from the sample; wherein the means for detecting includes means for detecting a change in a phase dependent quantity of the transmitted or reflected radiation relative to the source radiation.

In a fourth aspect, the present invention provides an apparatus for investigating a sample, the apparatus comprising means for generating a beam of substantially continuous electromagnetic source radiation having a frequency in the range 25 GHz to 100 THz; means for moving the sample relative to the beam to scan the beam over the sample; means for detecting the radiation transmitted by or reflected from the sample; wherein the means for detecting includes means for comparing a phase dependent quantity of the transmitted or reflected radiation with that of the source radiation.

In a fifth aspect, the present invention provides an apparatus for investigating a sample, the apparatus comprising means for generating a beam of substantially continuous electromagnetic source radiation having at least two frequency components in the range from 25 GHz to 100 THz; means for detecting radiation transmitted by or reflected from the sample; wherein the means for detecting includes means for detecting a change in a phase dependent quantity of each frequency component of the transmitted or reflected radiation relative to the source radiation.

In a sixth aspect, the present invention provides an apparatus for investigating a sample, the apparatus comprising means for generating a beam of substantially continuous electromagnetic source radiation having at least two frequency components in the range from 25 GHz to 100 THz; means for detecting radiation transmitted by or reflected from the sample; wherein the means for detecting includes means for comparing a phase dependent quantity of each frequency component of the transmitted or reflected radiation with that of the source radiation.

BRIEF DESCRIPTION OF THE DRAWINGS

Thus, the present invention can be used for both imaging a sample and also studying the spectra of a sample at a point.

The present invention will now be described with reference to the following non-limiting preferred embodiments in which:

FIGS. 10, 10a and 10b show a detector which may be used with either of the imaging systems of FIG. 1 or 2;

DETAILED DESCRIPTION OF THE INVENTION

Figure 1:
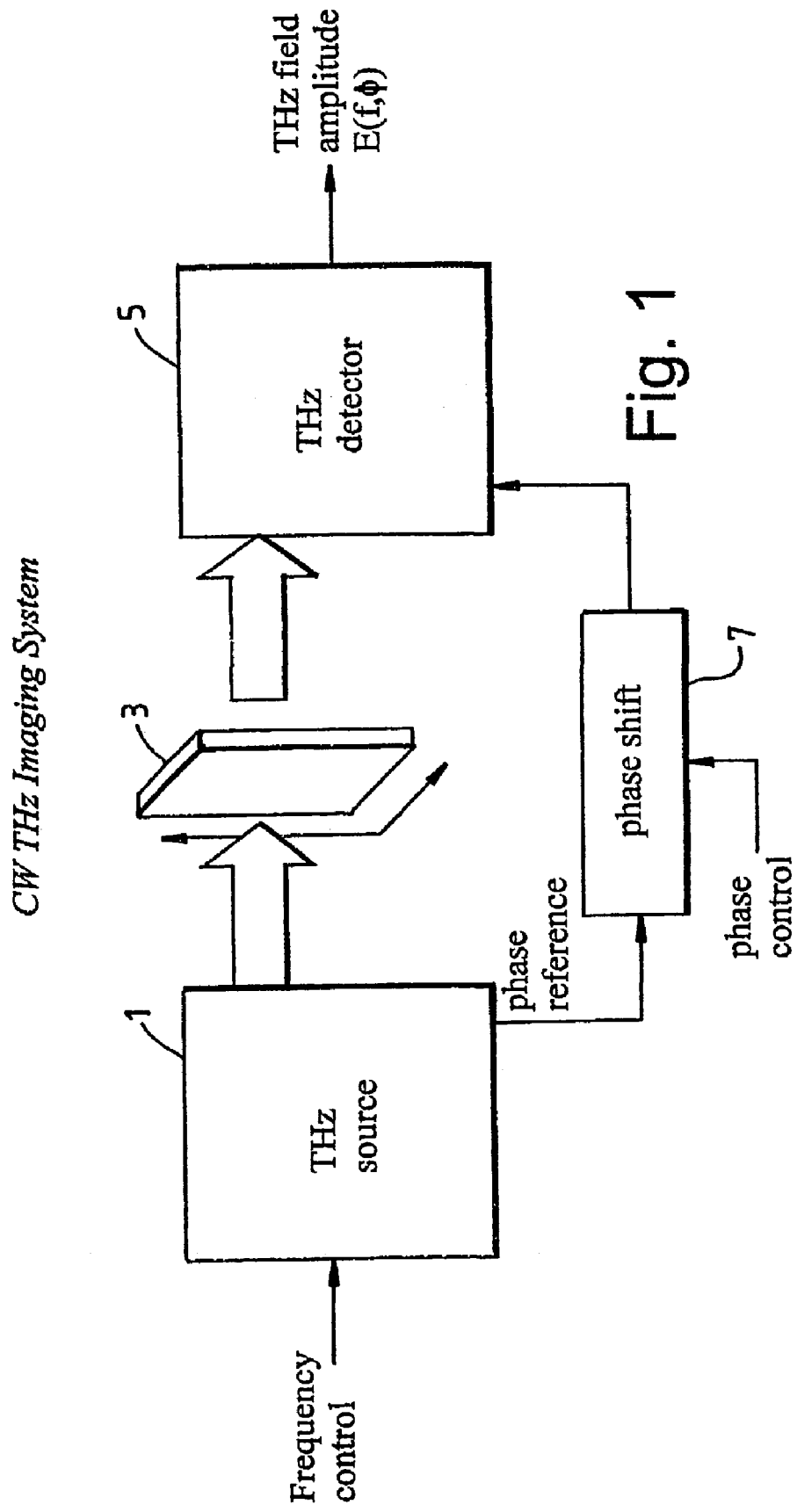
FIG. 1 shows a schematic imaging system in accordance with an embodiment of the present invention.

In the imaging system of FIG. 1, radiation is generated from THz generator 1. THz generator 1, generates terahertz radiation with a single frequency in the range from 0.025 THz to 100 THz. (Details of THz generator 1 will be described with reference to FIGS. 3 to 9.) The THz radiation emitted from the generator 1 irradiates sample 3.

Sample 3 is located on a stage (not shown), the stage is capable of moving sample 3 through the beam of radiation emitted from generator 1 in the x and y directions. The x and y directions being taken as two orthogonal directions which are substantially perpendicular to the path of the incident irradiating radiation from the source 1.

Sample 3 will both transmit and reflect radiation. In the specific example of FIG. 1, the sample is only shown to transmit radiation and only transmitted radiation will be detected. However, reflection measurements are possible.

The transmitted radiation is detected by detector 5. (Examples of the types of detector which may be used will be described with reference to FIGS. 10 and 11. Further variations on the imaging system and detector will also be described with reference to FIGS. 12 to 22).

The detector 5 is used to detect both the amplitude and phase of the radiation emitted from the sample 3. In order to do this, there is a phase coupling/control means 7 provided between the detector (or an input to the detector) and the generator 1 or an input/output from generator 1. This phase control/coupling means will either provide the detector with a parameter corresponding to a phase input which can be varied relative to the source beam or it will vary the phase of the source beam with respect to a probe beam which will be supplied to an input of the detector.

Typically, a beam, a 'probe beam' with a known phase relationship to that of the imaging radiation is fed into the phase coupling/control means 7. The phase coupling control means will typically comprise a variable optical path line which will allow the path length of the probe beam to be varied.

In many cases, the probe beam will be combined with the THz radiation which is transmitted through the sample 3. One particularly popular way is to use electro-optic sampling (EOS). This type of detector will be described in more detail with respect to FIG. 10.

An explanation of how the phase and amplitude of the transmitted radiation is detected will be described for use with EOS detection. However, it will be apparent to those skilled in the art that this type of analysis could be performed for any type of detector.

In this type of detector, the THz beam and the probe beam co-linearly propagate through a detection member. The transmitted THz electric field passes through this member and will be referred to as $E_{THz}(t)$. The intensity of the probe beam is $I_{probe}(t)$. The transmitted radiation from the sample 3 passes through the detection member and modulates the probe beam. The emitted probe beam intensity can be written:

$$\Delta I_{eo}(t) \alpha I_{probe}(t) E_{THz}(t).$$

$$I_{probe}(t) = I^0_{opt}[A + \cos(\omega_{THz} t - \phi_p)]$$

Where $I^0_{opt}$ is the maximum intensity of the probe beam, A is a constant, $\omega_{THz}$ is the frequency of the THz radiation and $\phi_p$ is the phase of the probe beam.

$$E_{THz}(t) = E_{THz} \cos(\omega t - \phi_{THz}).$$

Where $E_{THz}$ varies as $I^0_{opt}$; and $\phi_{THz}$ is the phase of the THz radiation.

Hence $$\Delta I_{eo} \alpha I_{opt} E_{THz} \cos(\phi_{THz} - \phi_p) \qquad (1)$$

$E_{THz}$ and $\phi_{THz}$ will depend on the sample. Therefore, by varying $\phi_{THz} - \phi_p$, it is possible to determine $E_{THz}$ and $\phi_{THz}$. It should be noted that either $\phi_p$ or $\phi_{THz}$ can be varied. The change in $\phi_{THz}$ due to the sample will be a constant for a fixed frequency.

Further, varying the quantity $\phi_{THz} - \phi_p$ allows the time of flight of the THz pulse through the sample to be determined.

The phase of the Terahertz beam, $\phi_{THz} = \omega.n_t.d_t/c$ and the phase of the probe beam is $\phi_p = \omega_{THz} n_p d_p/c$ Where $n_{THz}$ and $n_p$ are the refractive index (or indices) associated with the path lengths of THz and probe, respectively. $d_t$ and $d_p$ are the path lengths associated with the THz and probe, respectively.

$\Delta\phi = \phi_{THz} - \phi_p$ may be measured using photoconductive, EOS or other detection techniques where the detector has phase knowledge of the generated THz. In the case of photoconductive of EOS techniques, these detection techniques may applied to coherently generated THz, and may be used to deduce the width and refractive index of the medium. This is because in the most general case, $\Delta\phi = \phi_{THz} - \phi p$ may be written as $$\Delta\phi = \phi_{THz} - \phi_p = \omega_{THz}/c(d_t n_t - d_p n_p)$$

which obtains explicit expression for the refractive index or indices $n_t$ and path lengths (thickness) $d_t$ of the sample 3.

The cosine dependence of Eq. (1) implies that as one of the path lengths (say $d_p$) is changed, a maximum in the measured signal occurs whenever $$2\pi i = \alpha\phi = \omega_{THz}/c(d_t n_t - d_p n_p)$$

where i is an integer denoting the $i^{th}$ oscillation, and $$d_p n_t = ic/f_{THz} + d_p n_p, f_{THz} = \omega_{THz}/2\pi.$$

Because $f_{THz} = (f_1 - f_2)$ is known accurately from the optical/near-IR frequencies, or by conventional calibration means in the case of electronic sources such as Gunn diodes, and $d_p$ (determined by the delay in the probe beam) and $n_p$ (typically=1 for free space) are accurately known, it is possible to determine $d_t$ and $n_t$ of the object under study at each pixel in the image.

By moving the sample through the THz beam, or alternatively scanning the beam across the sample, it is possible to build up refractive index or thickness image of the object.

It is also possible to build up transmission or absorption images of the sample using information from the detected $E_{THz}$.

This may be done in transmission, reflection, or a combination of the two. For the case of the refractive index, panchromatic images are additionally possible (in addition to the monochromatic image described above) by tuning $\omega_{THz}$ to different values at each pixel. Where the THz radiation is produced by converting the frequency of one or more input beams in radiation within the THz range, it is possible to sweep the frequency of one or more of the input beams. The emitted THz radiation may be tuned, for example, by varying the frequency of one of the near IR/visible diodes if photoconductive or difference frequency generation means are utilised in generation, or alternatively by voltage tuning or cavity tuning of electronic devices such as Gunn diodes are utilised.

There are a variety of ways to obtain an image of sample 3:

1) Monochromatic transmission/absorption:

The delay of the probe beam ($d_p$), which is essentially one way of sweeping the phase of the detector relative to the source, may be swept at each pixel, and the measured peak amplitude may be plotted at each pixel as the object is rastered through the beam (or the beam through the object). Alternatively, the absorption coefficient may be extracted from the ratio of the peak amplitude to that of a reference e.g. free space and then plotted for each pixel.

2) Panchromatic transmission/absorption: As for 1) except, it is performed for a variety of different THz frequencies $\omega_{THz}$. Individual monochromatic images may be compared, ratioed, subtracted, added etc. Alternatively the transmission or absorption at each pixel may be integrated over a range of measurement each at different $\omega_{THz}$.

3) Thickness of the image. The probe delay $d_p$ as explained with reference to 1) above may be swept at each pixel and the product $d_t n_t$ may be extracted from suitable manipulation of the above equations. $d_t$ so obtained at each pixel using pre-determined $n_t$ can be plotted across the sample to build up a thickness (tomographic) image.

4) Refractive index image: Manipulation of the above equations measuring phase, $n_t$ can be plotted using a fixed $d_t$. Monochromatic (at single $\omega_{THz}$) and/or panchromatic (over a multitude of $\omega_{THz}$ analogus to point 2) above) images may be used.

5) Alternatively, a fixed delay $d_p$ can be used. If $d_p$ and $n_p$ are fixed as well as $\omega_{THz}$ the sample can be rastered through the beam (or vice versa). All variations in the image produced are either due to changes in the thickness of the object, the refractive index of the object or due to changes in absorption of the object.

Figure 2:
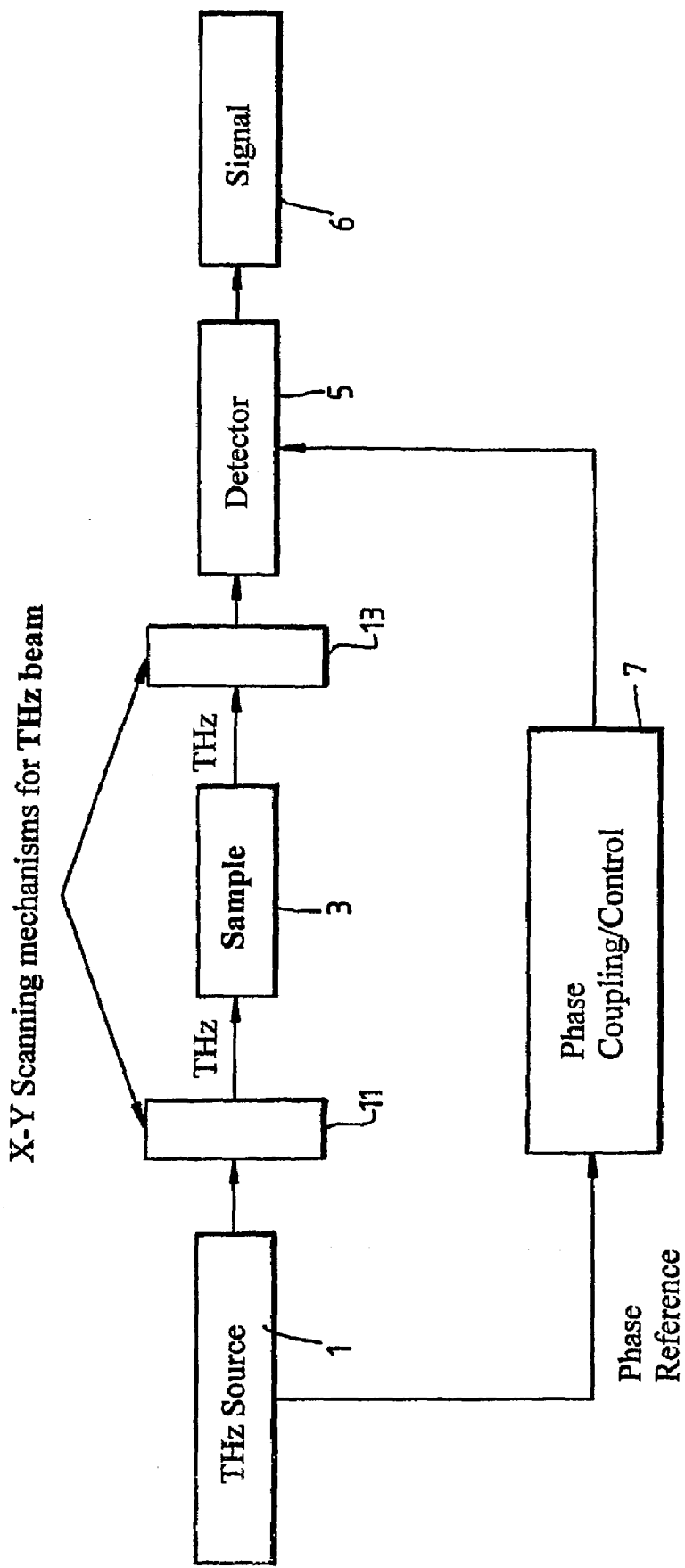
FIG. 2 shows a variation of the imaging system of FIG. 1.

FIG. 2 shows a further variation on the imaging system of FIG. 1. As for FIG. 1, the imaging system comprises a generator 1 which irradiates a sample 3. Radiation which is transmitted or reflected by the sample 3 is then detected by detector 5, to output signal 6. The detector 5 is configured to be able to detect a phase dependent quantity of the detected radiation via phase coupling/control means 7 which serves to input a signal into the detector concerning the phase of the radiation emitted from the generator.

In this example, the sample 3 remains fixed and the incident radiation beam is swept in the x and y direction with respect to the sample. A beam sweeping stage 11 is positioned between the generator 1 and the sample 3, this serves to 'raster' the incident radiation across the surface of the sample. A beam detection stage 13 is located between the sample 3 and the detector 5. The beam detection stages sweeps detection optics used to detect radiation transmitted through the sample 3 with the beam irradiating the sample 3. Usually, the beam sweeping stage 11 and the beam detection stage 13 will be swept together using the same stepper motor to ensure that both stages move together. In some instances such as if the detector is based on CCD or Terahertz imaging arrays of mixers, it may not be necessary to have stage 13.

Figure 3:
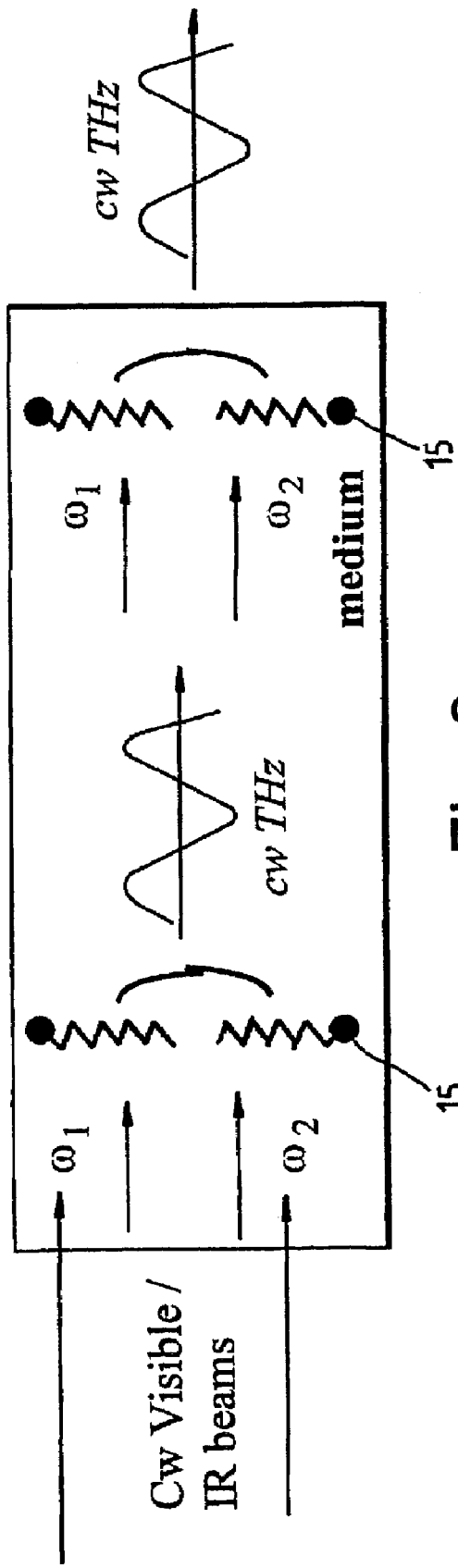
FIG. 3 is a schematic generator which may be used in either of the imaging systems of FIGS. 1 and 2.

FIG. 3 shows a so-called χ(2) method for producing THz radiation. The generator 1 in both of FIGS. 1 and 2 could work using this principle.

Typically, the Polarisation of a medium can be written as:

$$P \alpha \chi E$$

Where $\chi$ is the polarisability of the medium and E is the incident electric field. In reality the polarization should be written as:

$$P \alpha \chi E + \chi^{(2)} E^2 + \chi^{(3)} E^3$$ etc. In many materials, the higher order terms such as $\chi^{(2)}$ will be negligible, but in some materials and especially non-centrosymmetric crystals, they will be significant.

A large $\chi^{(2)}$ can manifest itself in a number of ways. If such a crystal is irradiated with a single frequency then the second harmonic of the frequency can be emitted by the crystal. If the crystal is irradiated by the different frequencies $\omega_1$ and $\omega_2$, radiation having a frequency which is the difference or the sum of these frequencies is outputted. Which will depend on the configuration and properties of the crystals.

FIG. 3 shows such an arrangement. The electrons in the non-linear material which will be referred to as the 'frequency conversion member' 15 can be thought of as being on springs. As the frequency conversion member 15 is irradiated with visible or infra red radiation $\omega_1$ and $\omega_2$, the electrons vibrate to emit radiation with a THz frequency, the THz radiation $\omega_{THz} = \omega_1 - \omega_2$.

Typically, such frequency conversion member will have phase matching means in order to keep the transmitted THz signal and the incident radiation in phase as they pass through the frequency conversion member. Such phase matching can be achieved by providing the frequency conversion member with a variation in its refractive index configured to keep the two signals in phase (at all points) as they pass through the frequency conversion member.

Figure 4:
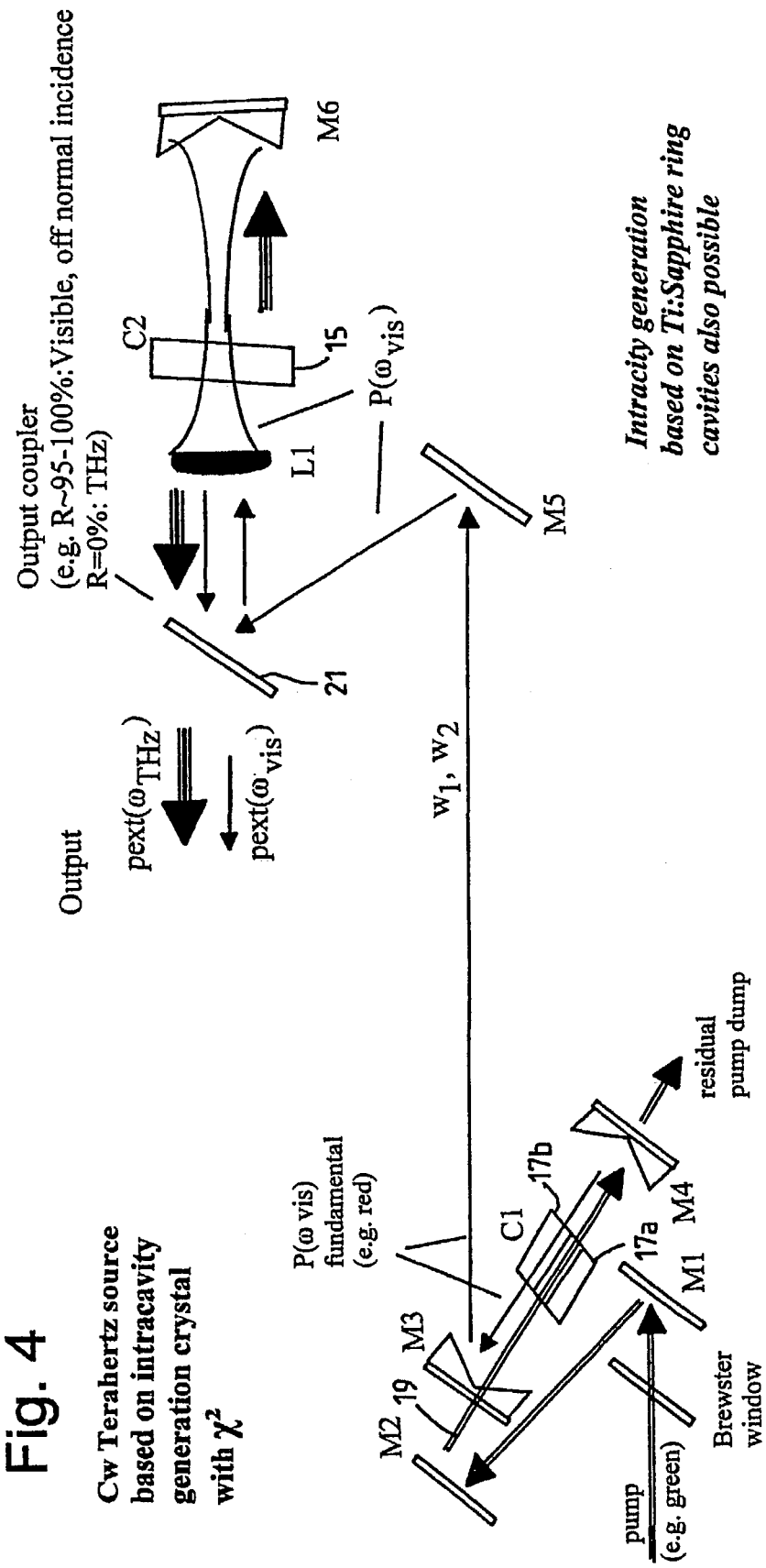
FIG. 4 shows a generator which may be used in either of the imaging systems of FIGS. 1 and 2.

FIG. 4 shows a THz generator using a frequency conversion member as described above. The radiation used to generate the THz radiation via frequency conversion member 15. Radiation is supplied to frequency conversion member 15 from Ti:Sapphire crystals 17a and 17b. Ti:Sapphire crystal 17a emits radiation with a frequency of $\omega_1$ (the first pump beam) in response to radiation with laser driving beam 19 and Ti:Sapphire crystal 17b emits radiation with a frequency $\omega_2$ (the second pump beam) in response to irradiation with pump beam 19. In order to provide efficient lasing, it is desirable to continually reflect the first and second pump beams onto Ti:Sapphire crystals 17a and 17b. Therefore, the lasing crystals 17a and 17b are typically provided within a lasing cavity.

The driving beam 19 is directed onto crystals 17a and 17b using mirrors M1 and M2. The driving beam 19 can pass through mirror M3 and onto lasing crystals 17a and 17b. The driving beam 19 which is not absorbed by crystals 17a and 17b, is emitted through mirror M4. Mirror M4 serves to reflect any radiation with frequencies $\omega_1$ and $\omega_2$ back onto the lasing crystals 17a and 17b. This radiation is then reflected via mirror M3 onto mirror M5 and onto output coupler 21. Output coupler 21 serves to reflect radiation with the frequencies $\omega_1$ and $\omega_2$ onto the frequency conversion member 15 to produce $\omega_{THz} = \omega_1 - \omega_2$. The pump beams are focused onto frequency conversion member 15 via lens L1. Any radiation which is transmitted through the frequency conversion member 15 is reflected back through the frequency conversion member 15 by mirror 6. This radiation then impinges on output coupler 21.

Output coupler 21 transmits radiation with the frequency $\omega_{THz}$, but it reflects light with the frequencies $\omega_1$ and $\omega_2$ back onto mirror M5, which in turn reflects the radiation back onto the lasing crystals 17a and 17b via mirror M3. In other words, the lasing crystals 17a, 17b and the frequency conversion member 15 are all located within the same lasing cavity defined by mirror M6, the output coupler and mirrors M5, M3 and M4. Radiation with frequencies $\omega_1$ and $\omega_2$ are constantly reflected within this cavity to efficiently generate the pump beams and the THz beam.

Figure 5:
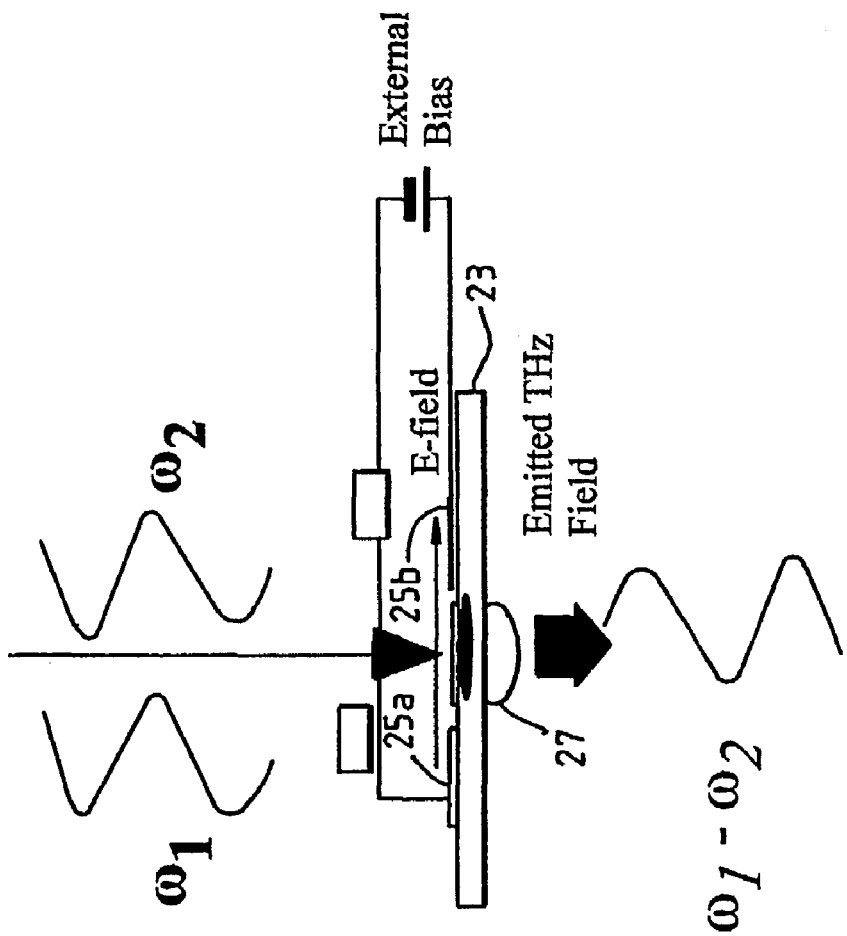
FIG. 5 shows a generator which may be used with either of the imaging systems of FIGS. 1 and 2.

Other types of generator may also be used. FIG. 5 illustrates a so-called photoconductive emitter. The emitter comprises a member 23 comprising a semiconductor such as low temperature GaAs, GaAs, Si on Sapphire etc. The semiconductor member has a pair of electrodes 25a and 25b located on its surface. The electrodes 25a and 25b are connected to a power supply such that a field can be generated between the two electrodes 25a and 25b.

The simplest electrode arrangement is show in FIG. 5. However, the electrodes may be triangular and arranged in a bow-tie shape, a so-called bow-tie antenna or they may be interdigitated electrodes at the centre of a bow tie or spiral antenna. Alternatively, such designs may be incorporated into transmission lines on the chip.

The semiconductor member is irradiated by two pump beams with frequencies $\omega_1$ and $\omega_2$. The pump beams impinge on the semiconductor member 23 on the part of its surface between the electrodes 25a and 25b, i.e. where the field is applied. The beating of the two visible or near-infrared lasers in the non-linear region of the semiconductor member between the two electrodes 25a and 25b results in the emission of THz radiation from the semiconductor member 23. The semiconductor member 23 is provided with a lens 27, which may be of a hemispherical or other design, on its surface which is opposite to that of the surface with the electrodes, to allow the emission of a beam of THz radiation.

Figure 6:
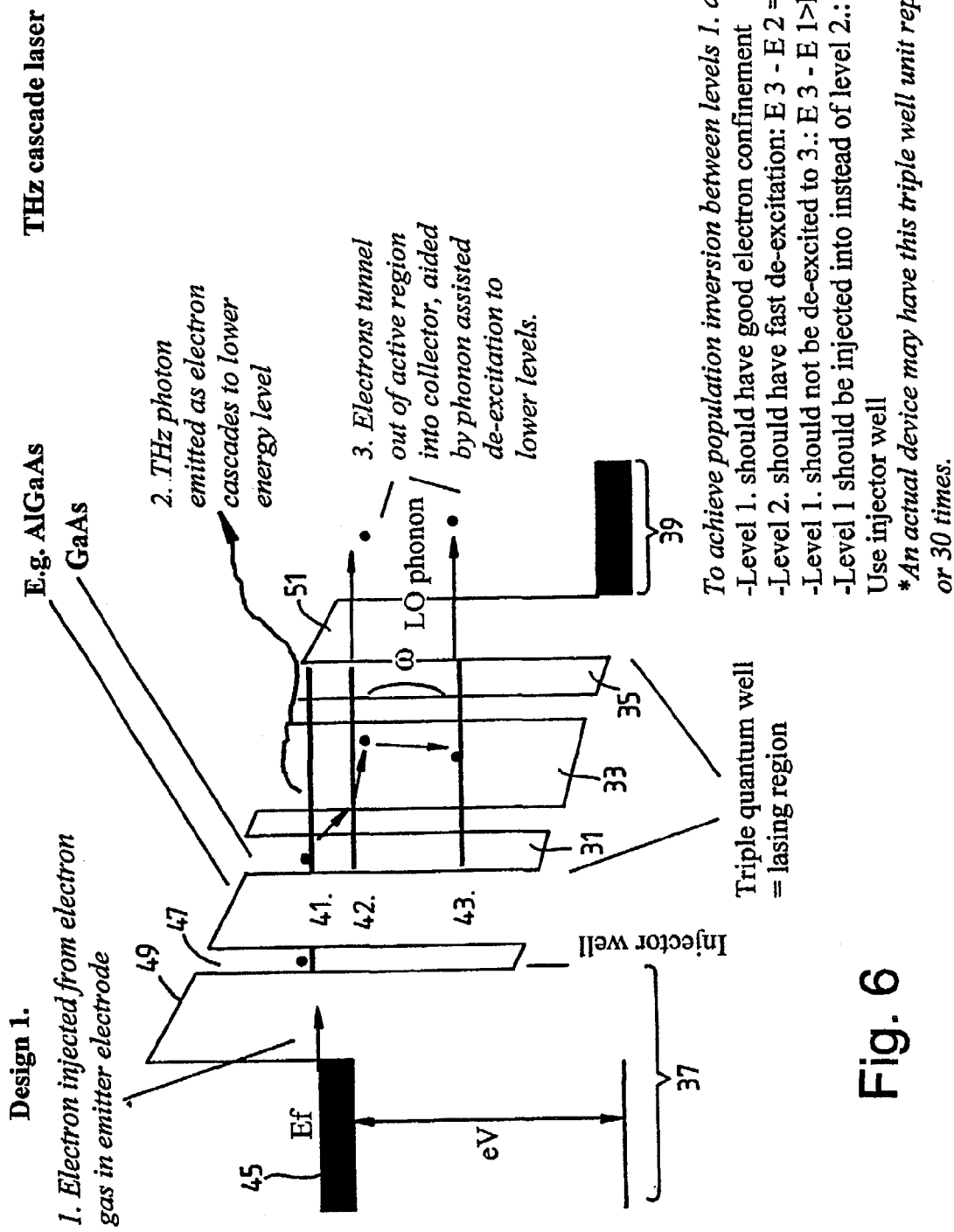
FIG. 6 shows a generator which may be used with either of the imaging system of FIGS. 1 and 2.

FIG. 6 shows a further type of generator. This is a so-called cascade laser which directly generates the THz radiation from the application of a bias i.e. there is no need to supply a pump-beam. The cascade laser uses three coupled quantum wells 31, 33 and 35 interposed between an emitter 37 and a collector 39. Possible layer structures for the laser will be discussed with reference to FIG. 9.

FIG. 6 shows a conduction band of a cascade laser, the three quantum wells 31, 33 and 35 are coupled such that the excited energy levels extend across the three quantum wells. Three excited energy levels 41, 42 and 43 are populated and/or depopulated during the emission process. The emitter 37 comprises an emitter contact 45 separated from an injector quantum well 47 by emitter energy barrier 49. An electron from the emitter contact 45 tunnels through barrier 49 into injector quantum well 47.

The laser is configured such that the confined energy level in the injector quantum well 47 aligns with the highest energy level 41 of the triple quantum well arrangement 31, 33 and 35. This results in the electron in the injector quantum well 47 resonantly tunnelling into highest energy level 41 of the triple quantum well system 31, 33 and 35. The electron in this energy level relaxes into the second energy level 42. During this process, it emits a photon with a wavelength in the THz range, in other words a THz photon. The electron which is now in the second level 42 will either be swept into the collector 39 through collector barrier layer 51, or it will relax further into the lowest energy level 43 of the quantum well structure, emitting an phonon and then tunnel through collector barrier 51 into the collector contact 39.

Figure 7:
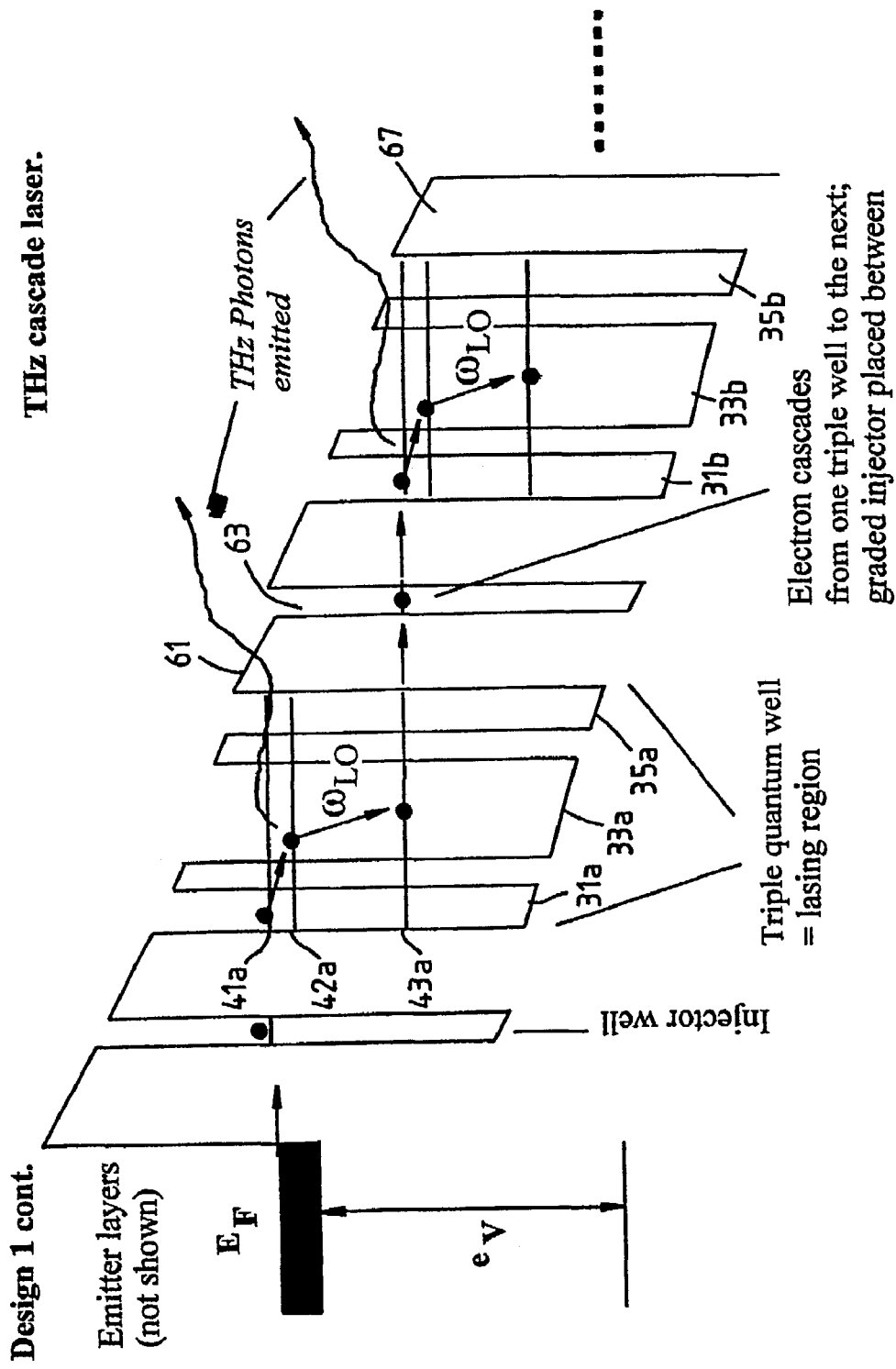
FIG. 7 shows the generator of FIG. 6 in more detail.

In practice, the laser will contain a plurality of triple quantum well structures as shown in FIG. 7. Here, there are two triple quantum well structures 31*a*, 33*a*, 35*a* and 31*b*, 33*b*, 35*b*. As explained in relation of FIG. 6, an electron is injected into triple quantum well region 31*a*, 33*a*, 35*a* and a THz photon is emitted due to the electron relaxing from the highest energy level 41*a* and the middle energy level 42*a*. The electron will then relax via a phonon process into the lowest energy level 43*a*.

In the laser of FIG. 6, the electron tunnels into the collector via collector energy barrier 51. In FIG. 7, once the electron is in the lowest energy level 43*a*, it tunnels through energy barrier 61 into the second injector quantum well 63. Once in this well, the electron tunnels through energy barrier 65 into the highest level 41*b* of a second triple quantum well system 31*b*, 33*b*, 35*b* where the process is repeated. Once the electron reaches the lowest level 43*b* in this second quantum well structure, the electron tunnels through energy barrier 67 into third injector quantum well (not shown) and so on. Typically, there will be about 30 triple quantum well structures.

In FIGS. 6 and 7 the lasing region of the laser or the 'active region' is formed by a triple quantum well structure. However, it is possible to also fabricate a lasing region which has four or more quantum wells. This is shown in FIG. 8*a*. Here, the lasing region comprises 6 quantum wells. Providing that the wells are configured such that the difference in energy between two of the levels is such that this transition gives rise to emission of a THz photon then any number of quantum wells can be used. Once the electrons exit the active region 71 they tunnel into injector region 73 which serves to inject the electrons into second active region 75 for the process to begin again.

In FIG. 8*a*, electrons in the active region both emit THz and relax back into their lowest energy state. However, it is possible for this lower energy transition to be achieved by in the injector region as shown in FIG. 8*b*. Here, the electrons are only allowed to make a single transition in the active region 71. Using the reference numerals of FIG. 6, they are only allowed to tunnel from the highest level 41 to the middle layer 42. The electrons then tunnel into the injector region and relax from the middle level 42 into the lower level 43 ready for injection into the second active region 75 within the injector 73.

In all of the previous examples, the electrons in the injector have resonantly tunnelled into the highest energy level of the active region i.e. the energy of the carrier in the injector quantum well has been aligned with that of the highest energy of the lasing region. However, the electron could relax from a higher energy level in the injector into the highest energy level of the active region as shown in FIG. 8*c*.

Figure 8:
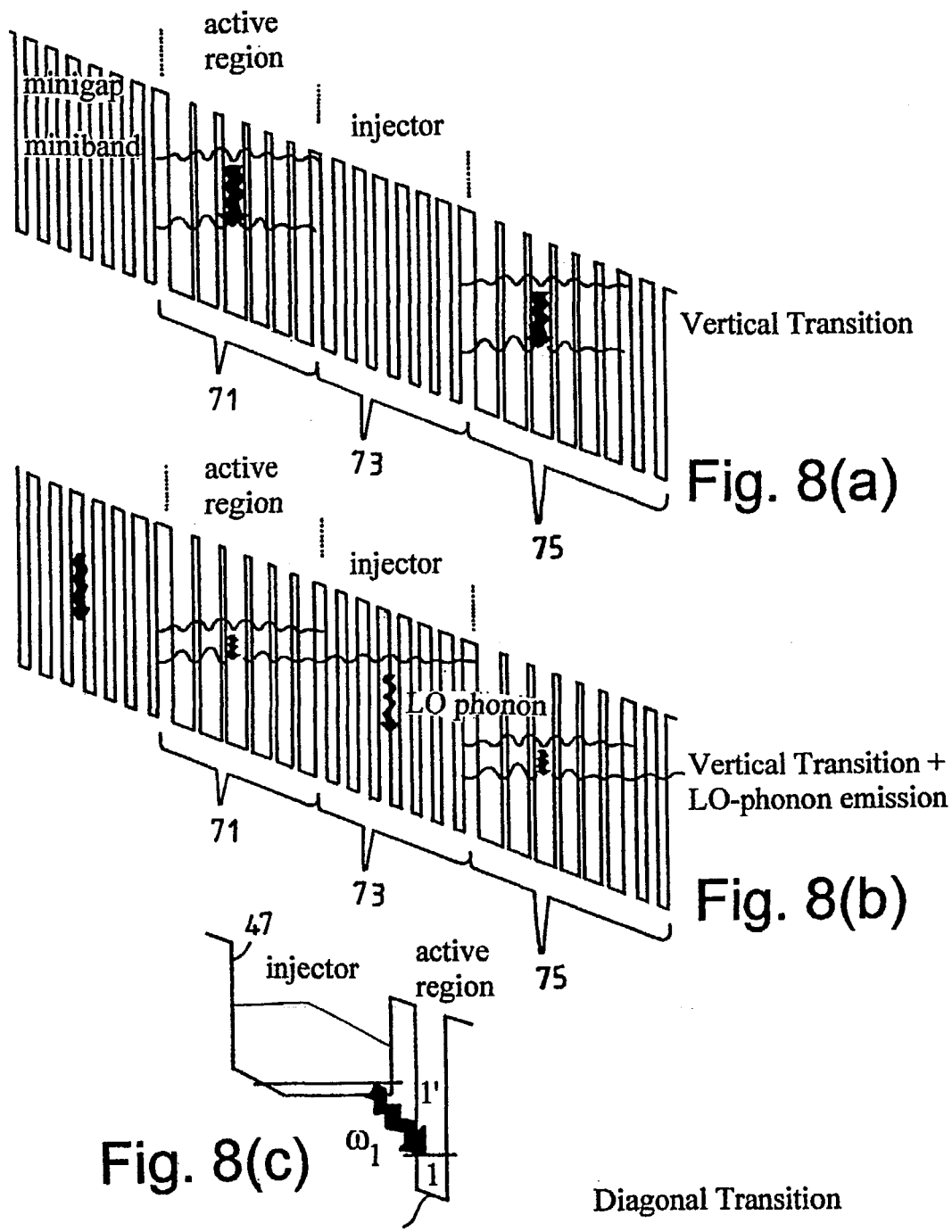
FIGS. 8a, 8b and 8c show further variations on the generators of FIGS. 6 and 7.
Figure 9:
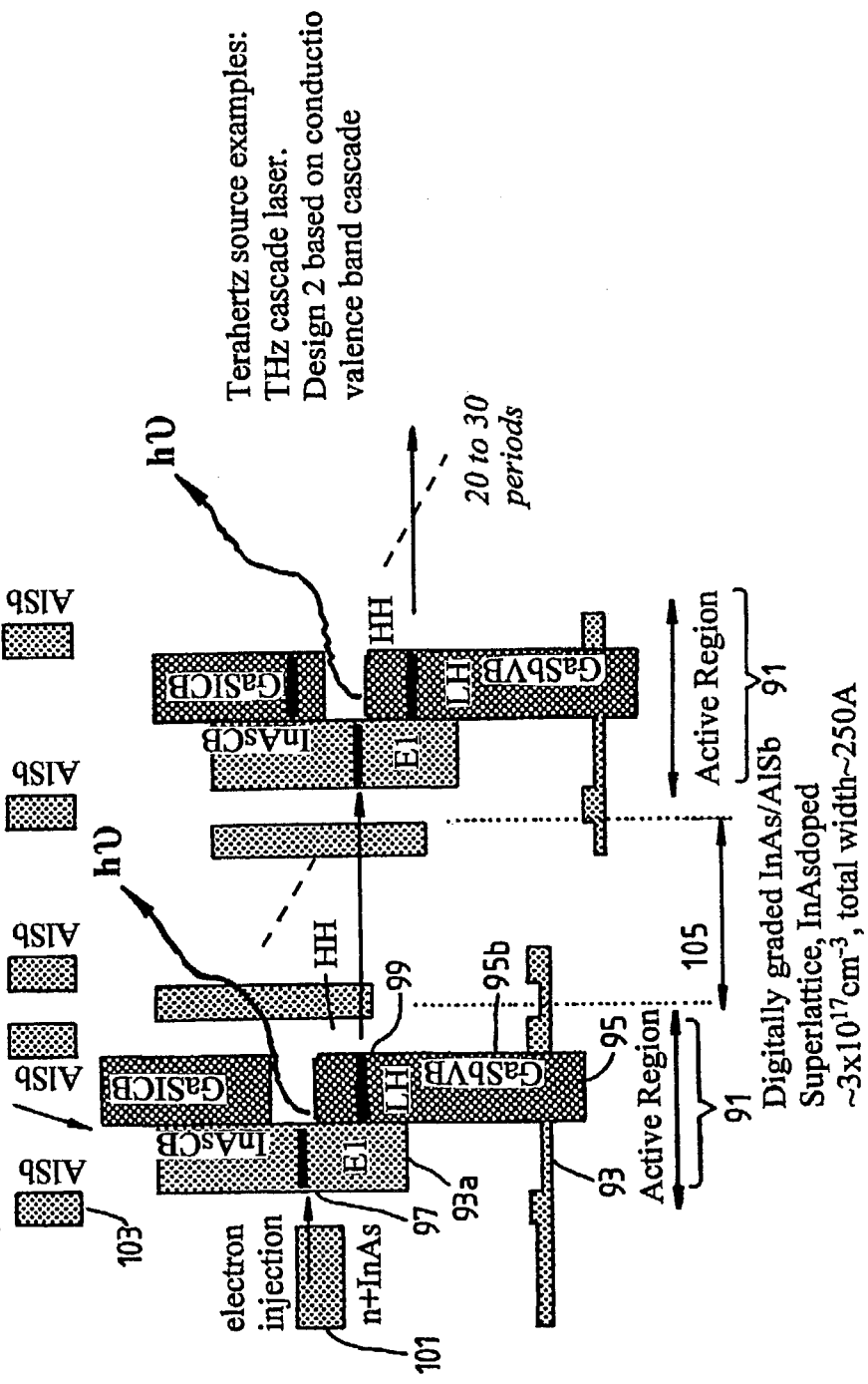
FIG. 9 shows a variation on the generator of FIG. 6.

FIG. 9 shows a further variation on the cascade laser of the FIGS. 6 to 8. In the above, the lasing region comprises three or more quantum wells and the all of the electron transitions have been intra-band transitions and specifically conduction band transitions.

FIG. 9 shows a cascade laser where the lasing region 91 is formed by two semiconductors which exhibit a type-II heterojunction. Initially, looking at the lasing region, 91, the region has a first semiconductor layer 93 located adjacent a second semiconductor layer 95. Possibly, a thin semiconductor barrier layer could be located between the first and second semiconductor layers. The first excited level 97 of the conduction band 93*a* in the first semiconductor layer 93 is located above a level 99 of the valence band 95*b* of the second semiconductor layer 95. The energy separation between conduction band level 97 and valence band level 99 is such that an electron relaxing from the upper level 97 to the lower level 99 causes the emission of a THz photon.

The other regions of the device remain essentially similar to those described with reference to FIG. 9, the electron is injected into level 97 from injector layer 101 which is separated from the lasing region by injector tunnel barrier 103. Once the electron exits level 99 it tunnels through the injector region 105 which in this example is a digitally graded super lattice.

A typical layer structure for example 9 would have the lasing region being formed from InAs and GaSb. The barrier layers could be formed from AlSb and the injector 101 could be n$^+$InAs. The superlattice 105 is formed from InAs/AlSb.

Figure 10:
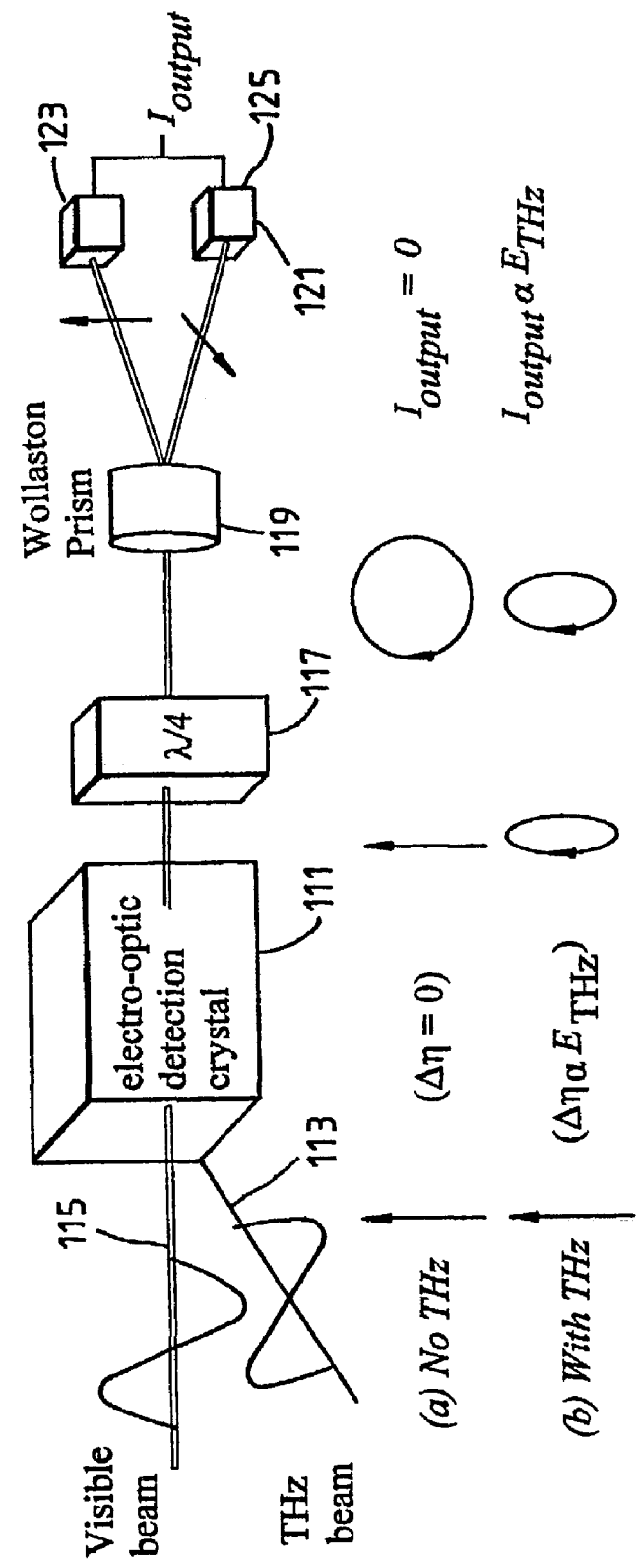
Figure 11:
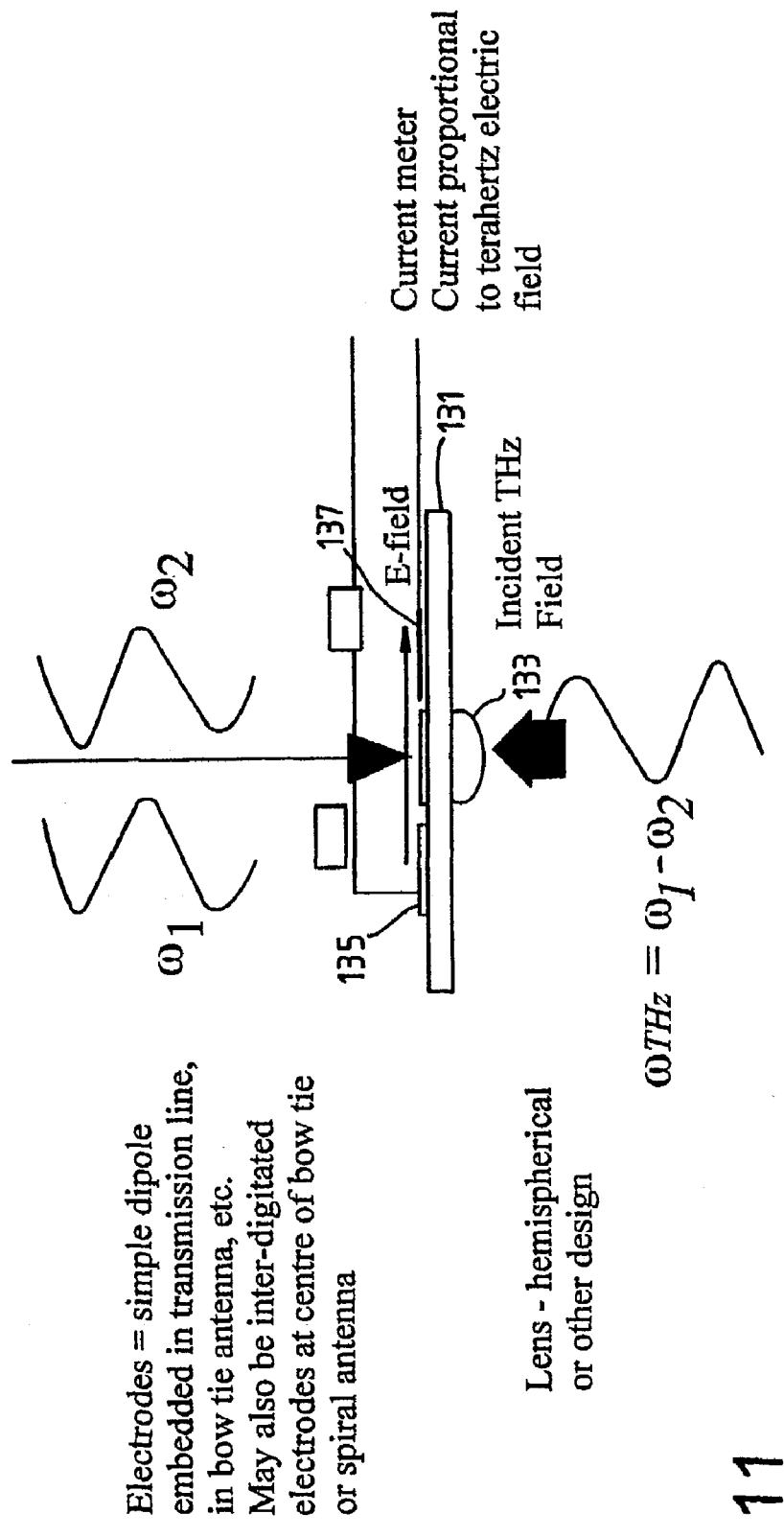
FIG. 11 shows a detector which may be used in accordance with either of the imaging systems of FIG. 1 or 2.

FIGS. 10 and 11 show typical detectors which can be used with the imaging systems of FIGS. 1 and 2.

FIG. 10 illustrates a possible detection mechanism which utilises the physical phenomenon known as the AC Pockels effect. The detector comprises a detection member 111. The transmitted THz radiation 113 from the sample 3 (FIG. 1) is detected by passing a visible beam or 'probe beam' 115 through the detection member 111 with the THz beam 113. The THz beam 113 modulates the birefringence of the detection crystal 111 as the AC Pockels effect gives:

$$\chi_0 E_0 + \chi^{(2)} E_0 E_{THz} \Rightarrow n_o + \Delta n(E_{THz})$$

Prior to entry into the detection member 111, the THz beam 113 and the probe beam 115 are polarised. FIG. 10*a* shows the situation where there is no THz beam. Here, the probe beam passes unaffected through the detection crystal 111. It is then passed into quarter wave plate 117. This serves to circularly polarise the emitted radiation as shown in FIG. 10*a*. The circularly polarised light is then fed through Wollaston prism 119 which divides the polarization of the light onto two orthogonal components. These two orthogonal components are then directed onto balanced photodiode assembly 121. The balanced photodiode assembly comprises two photo diodes 123,125 to respectively detect each of the orthogonal components from the Wollaston prism 119. The output of the photodiodes 123 and 125 are linked together such that the balanced photodiode assembly 121 only outputs an electrical signal if there is a difference between the readings of the two photodiodes 123, 125.

In the case of FIG. 10*a*, there is no difference between the two signals as there is no THz beam present. FIG. 10*b* shows the case where there is a THz beam 113. The THz beam 113 serves to make the radiation exiting the detection member 111 slightly elliptically polarised. This change in the polarization still remains after the radiation is passed through quarter waveplate 117. Extracting the orthogonal components of this radiation using prism 119 causes a different signal to be measured at the two photodiodes 123,125 and hence balanced photodiode assembly 121 outputs a signal corresponding to the strength of the THz field 113.

FIG. 11 shows a further example of a detector which may be used with the imaging systems of FIGS. 1 and 2. This type of detector is known as a photoconductive detector and comprises a detection member which may be, for example, GaAs, Si on Sapphire etc. The THz radiation is incident on the back surface of the detection member 131. The radiation is collected by lens 133 which may be hemispherical or have another shape. On the opposing side of the detection member 131 is located a pair of electrodes 135 and 137. The region between these two electrodes 135 and 137 is illuminated by radiation of the visible or near infrared range. As the detector needs to know information about the phase of the radiation emitted from the generator 1 (see FIG. 1), then this radiation preferably carries such information. Typically, the THz radiation which is used to image the sample will be described from this radiation. The near-infrared/visible radiation illuminates the surface of the detector between the electrodes 135 and 137. The Terahertz radiation which is collected by lens 133 induces a photocurrent through the region between the electrodes 135 and 137 which is being illuminated by the visible/infrared radiation. The current which can be detected by the electrodes is proportional to the strength of the THz field.

The electrode 135, 137 may be of a simple diode formation embedded in a transmission line. Alternatively, they may be triangular and arranged in the shape of a bow-tie to from a so-called bow-tie antenna. They may also be inter-digitated electrodes at the centre of a bow-tie or spiral antenna.

Figure 12:
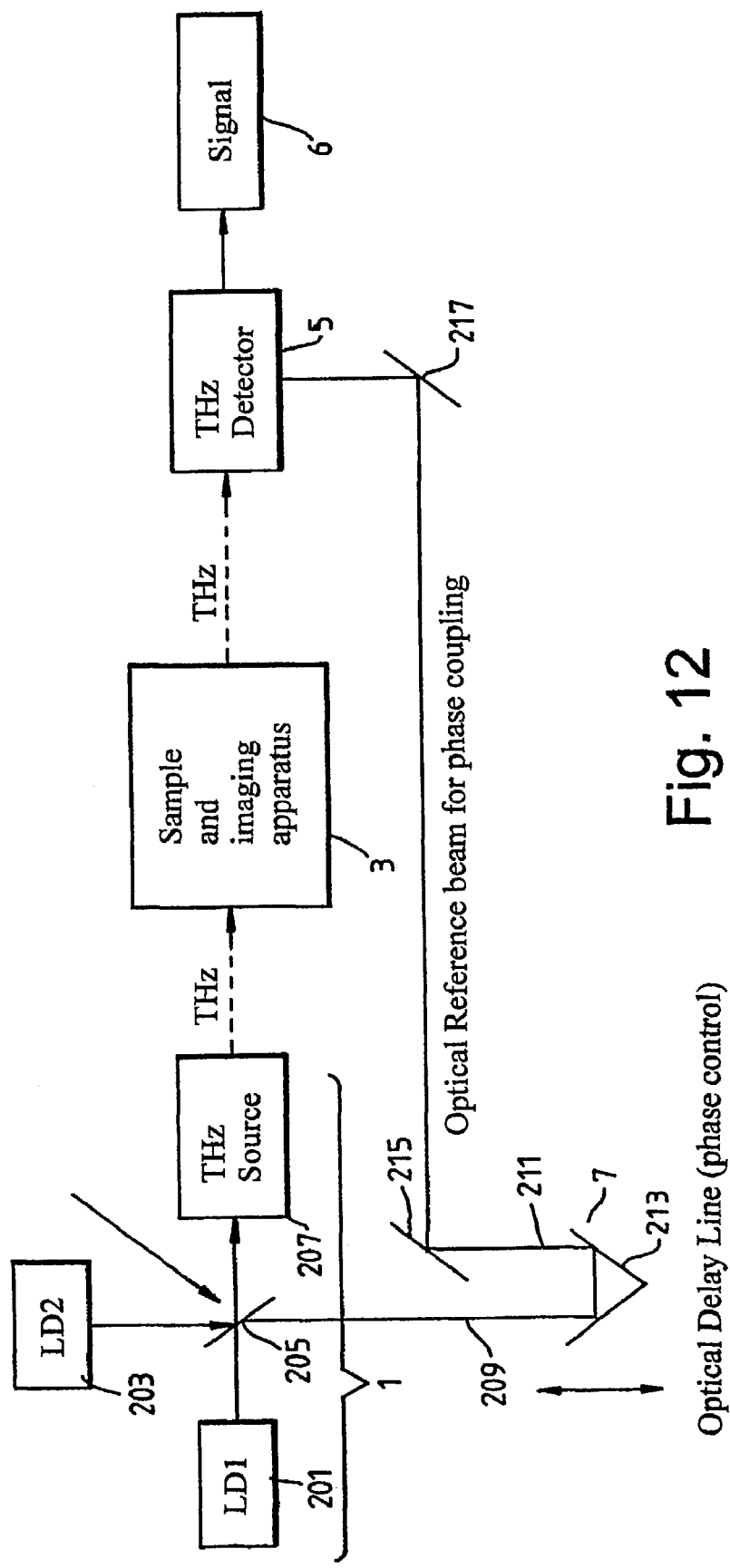
FIG. 12 shows an imaging system in accordance with an embodiment of the present invention, using diode lasers to generate the imaging radiation.

FIG. 12 shows a variation on the imaging system of FIGS. 1 and 2. To avoid unnecessary repetition, like reference numerals will be used to denote like features.

The THz generator 1 comprises two laser diodes 201, 203 which are configured to emit radiation with frequencies $\omega_1$ and $\omega_2$ respectively. The radiation emitted from both laser diodes 201 and 203 is combined using beam splitter/combiner 205. The combined radiation which contains both frequencies $\omega_1$ and $\omega_2$ is then directed into THz source 207 for emitting THz radiation. The THz radiation is produced with a frequency of $\omega_1-\omega_2$ and THz source 207 can use the difference frequency generation methods described with reference to FIGS. 3 to 5.

The beams emitted from laser diodes 201, 203 are taken as the probe beam 209 using beam splitter 205. This probe beam will be used to give the detector information about the phase of the radiation which is emitted from the THz source 1. The probe beam is fed into optical delay line 211 which is used as the phase coupling/control means explained with reference to FIG. 1.

In the optical delay line, the probe beam 209 is reflected off cube mirror 213 which is used to reflect the light through 180° and onto mirror 215 which in turn reflects the probe beam 209 into the detector 5 via the mirror 217.

Cube mirror 213 is moveable such that the path length of the probe beam can be varied as described with reference to FIG. 1. The probe beam is then directed into THz detector 5 which can be a detector as described with reference to with of FIGS. 11 and 12.

The sample and imaging apparatus 3 are configured such that either the sample can be moved with respect to the beam or the beam can be moved with respect to a stationary sample or both.

Improvements in the signal to noise ratio and hence acquisition times can be made by various modulation schemes. For example, dithering or oscillating of the mirror 213 will cause sinusoidal variations in the $d_p$ that can be detected using standard lock-in techniques. This is essentially a frequency modulation of the THz waveform as it is plotted out versus $d_p$. Similarly, it is possible to modulate the amplitude or frequencies of the sources outputting the radiation $\omega_1$ and $\omega_2$ to affect the amplitude and/or frequency modulation. This again results in noise suppression.

Figure 13:
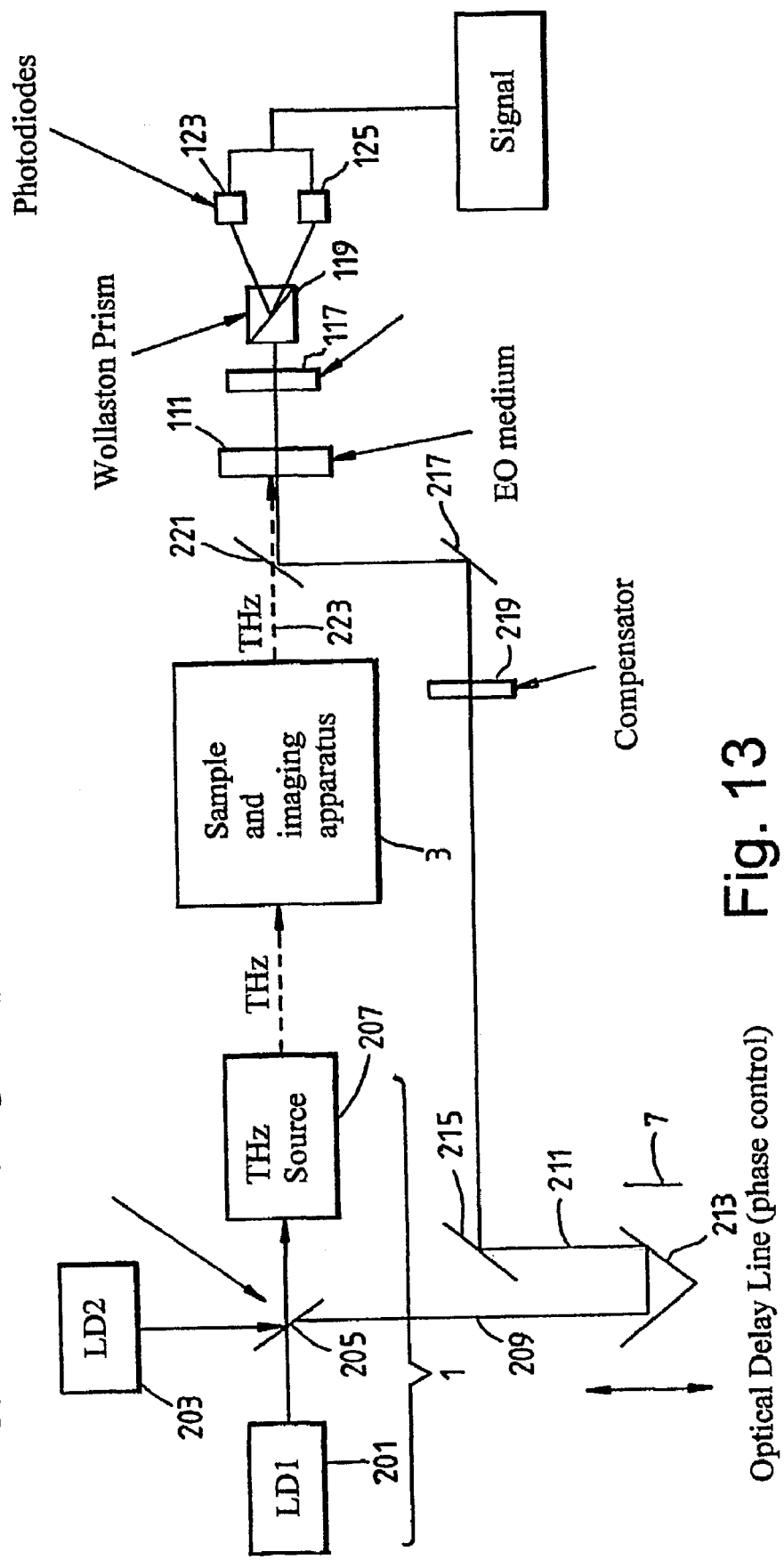
FIG. 13 shows an imaging system in accordance with an embodiment of the present invention using an electro-optic detection technique.

FIG. 13 shows a variation on the imaging system of FIG. 12. To avoid unnecessary repetition, like features will be denoted with like numerals. The generator 1, the sample and imaging apparatus and the optical delay line 211 are identical to that described with reference to FIG. 12. Prior to the probe beam being reflected from mirror 217, the beam is passed through compensator 219 to ensure the probe beam is polarised parallel to the THz beam 232. After reflection from mirror 217, the probe beam 209 is reflected onto beam combiner 221. Beam combiner 221 will typically be a mirror to reflect the probe beam 209 and having an aperture which can transmit the THz radiation 223 coming from the sample 3.

The combined probe 209 and Terahertz 223 beams are then directed onto detection member 111 which is identical to the member described with reference to FIG. 10. After the radiation has passed through the detection member, it is passed through the same optical and electrical elements described with relation to FIG. 10. The analysis of the data for this type of system where the phase coupling is achieved via an optical delay line and where the detector uses free space electro-optic sampling is set out in detail with relation to FIG. 1.

Figure 14:
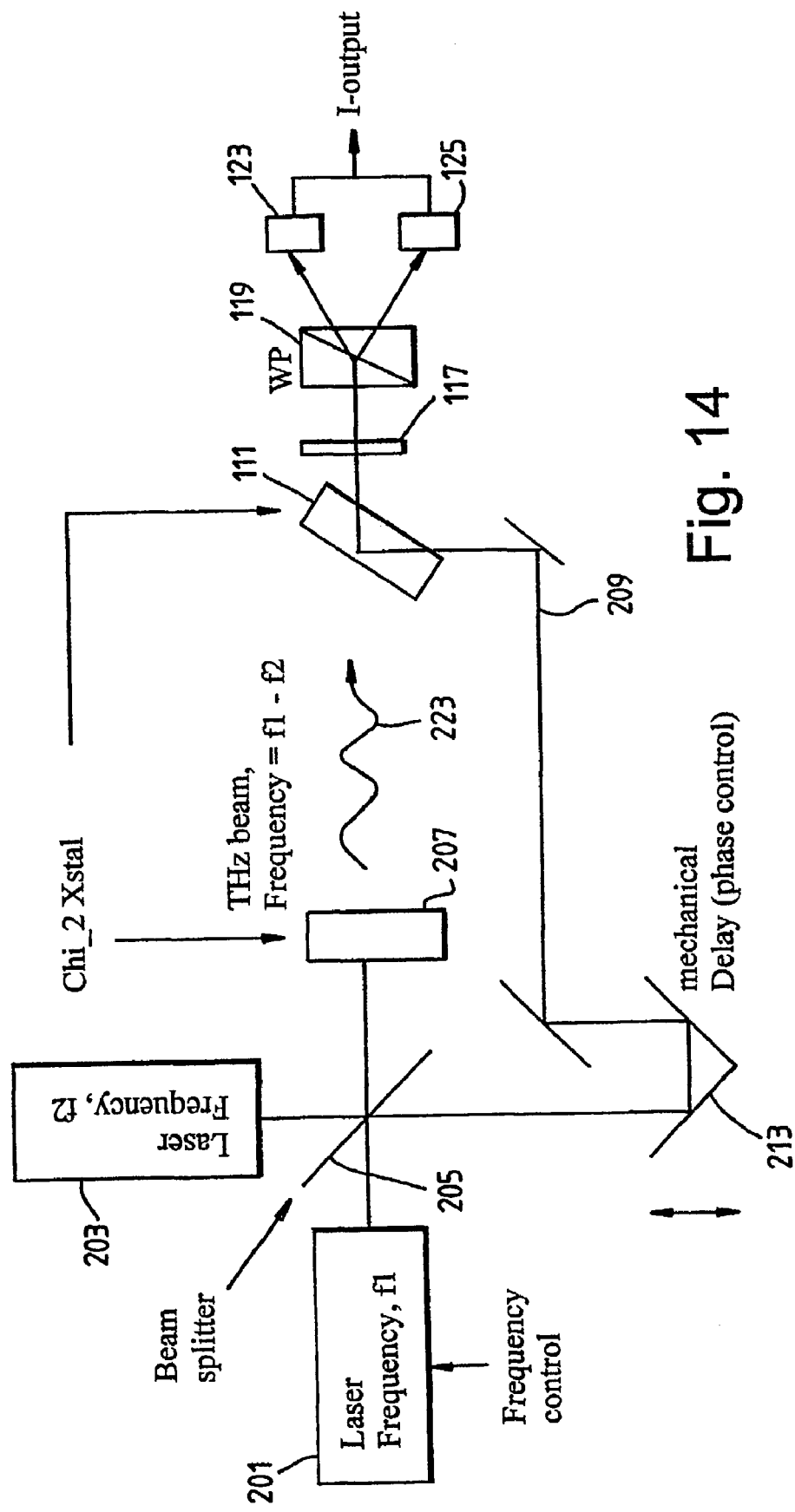
FIG. 14 shows an imaging system in accordance with an embodiment of the present invention using diode lasers and mixing elements.

FIG. 14 shows a slight variation on the imaging systems of FIGS. 12 and 13. As in FIGS. 12 and 13, radiation with frequencies $\omega_1$ and $\omega_2$ are produced respectively by laser diodes 201 and 203. The source comprises a $\chi^{(2)}$ frequency conversion member as explained with reference to FIG. 3. The source different from that of the FIGS. 12 and 13 as in this example, laser diode 201 has a variable frequency output and the emitted frequency can be chosen by applying a suitable bias to the diode. Also, it possible to sweep the frequency of the laser diode 203.

The THz beam which is transmitted through the sample impinges on the back of detection member 111 which is located at about 45° to the path of the transmitted THz beam 223. The detection member is also located at 45° to the path of the probe beam 209. The detection member 111 is provided with a reflective coating which is configured to reflect probe beam 209 such that the probe beam and the THz beam are combined within the detection member 111. The remaining optics have already been described in detail with reference to FIG. 3.

Figure 15:
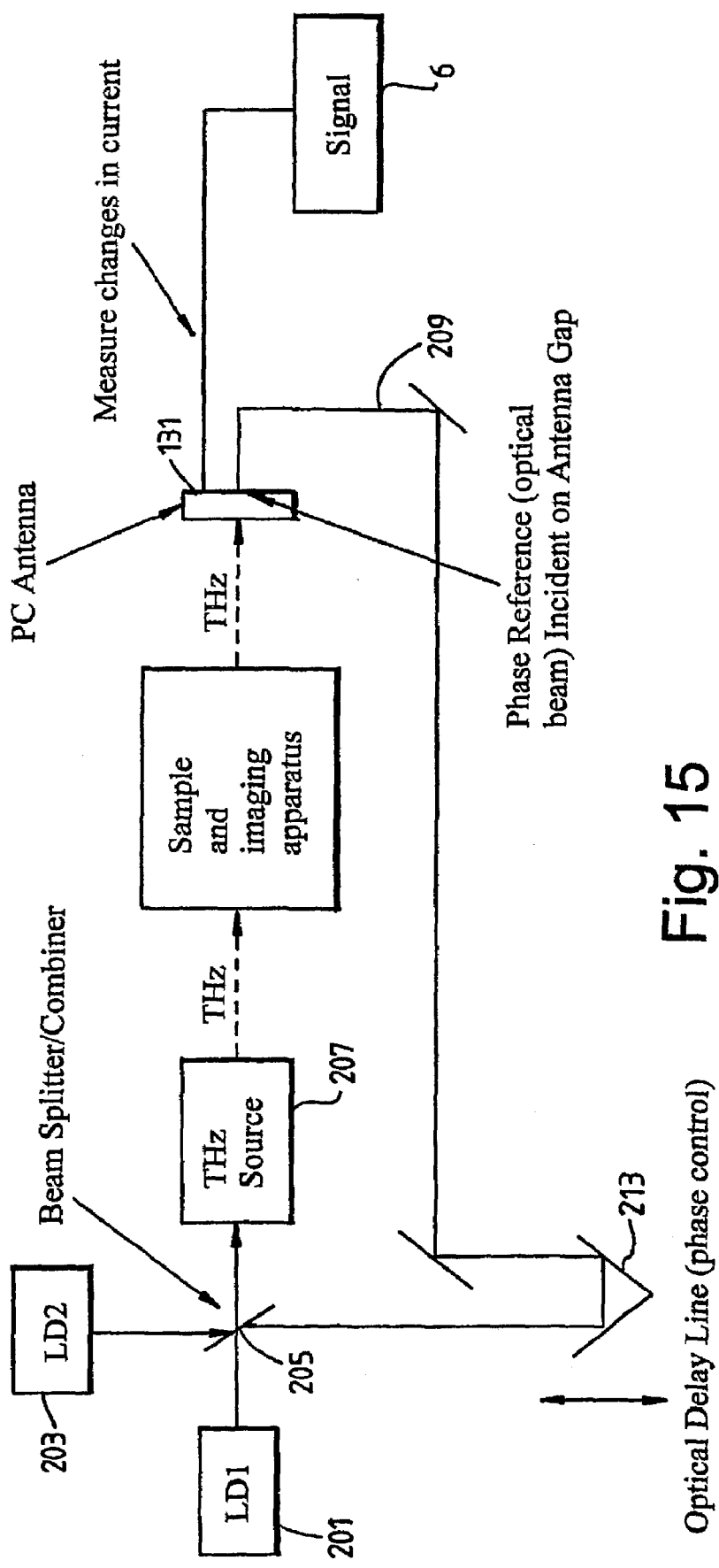
FIG. 15 shows an imaging system n accordance with an embodiment of the present invention using a photoconductive antenna as a detector.

FIG. 15 shows a variation on the imaging system of FIG. 12. The source, sample/imaging apparatus and optical delay line are the same. However, the detector here is a photo-conductive antenna which has been described with reference to FIG. 11.

Figure 16:
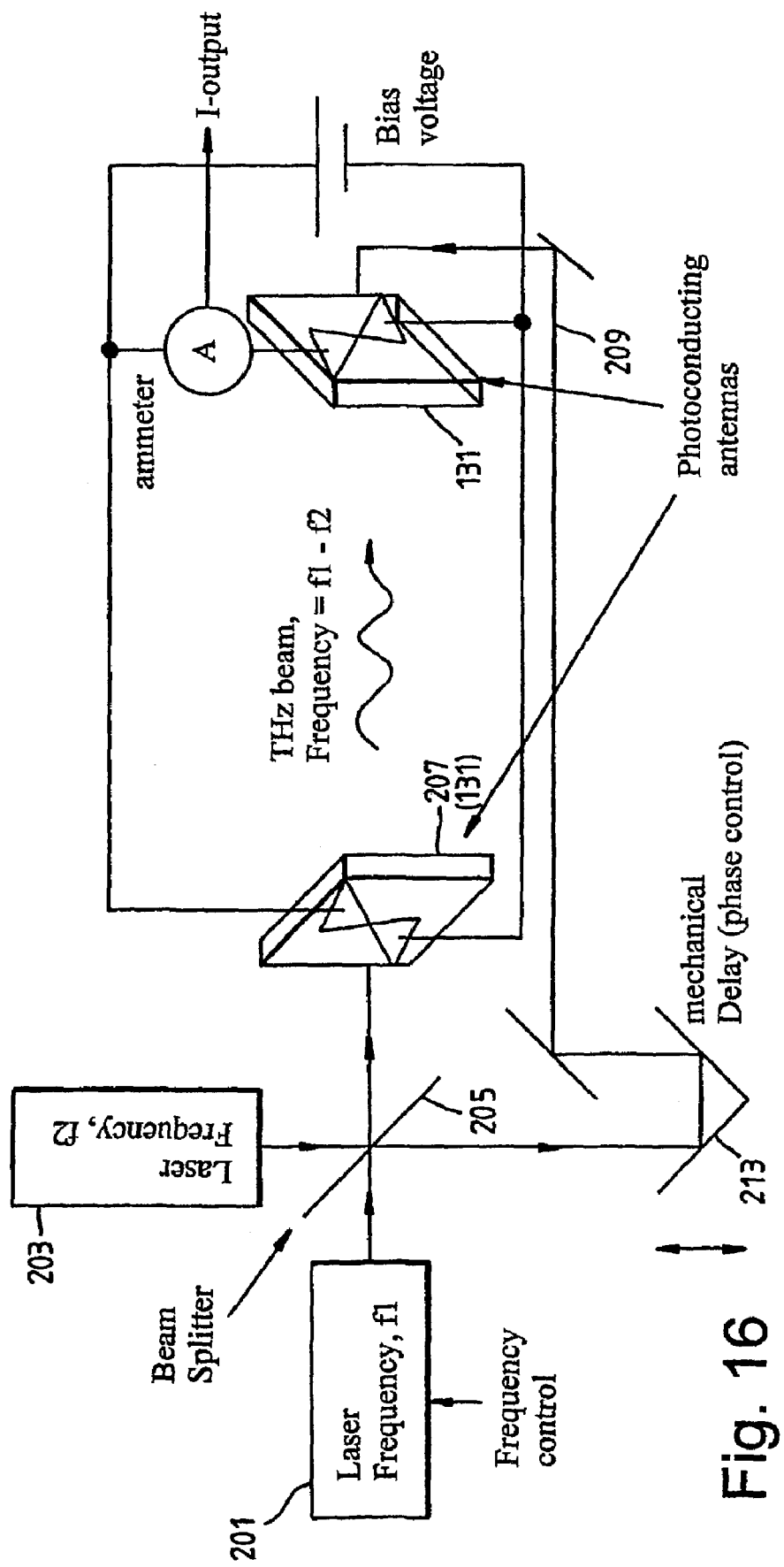
FIG. 16 shows an imaging system in accordance with an embodiment of the present invention using photoconducting antenna in both the generator and the detector.

FIG. 16 shows a variation on the imaging system of FIG. 15. Here, a photoconductive antenna is used to generate the THz radiation. This is described in detail with reference to FIG. 5. As described with reference to FIG. 14, the frequency of the first laser diode 201 can be varied with the application of a bias.

Figure 17:
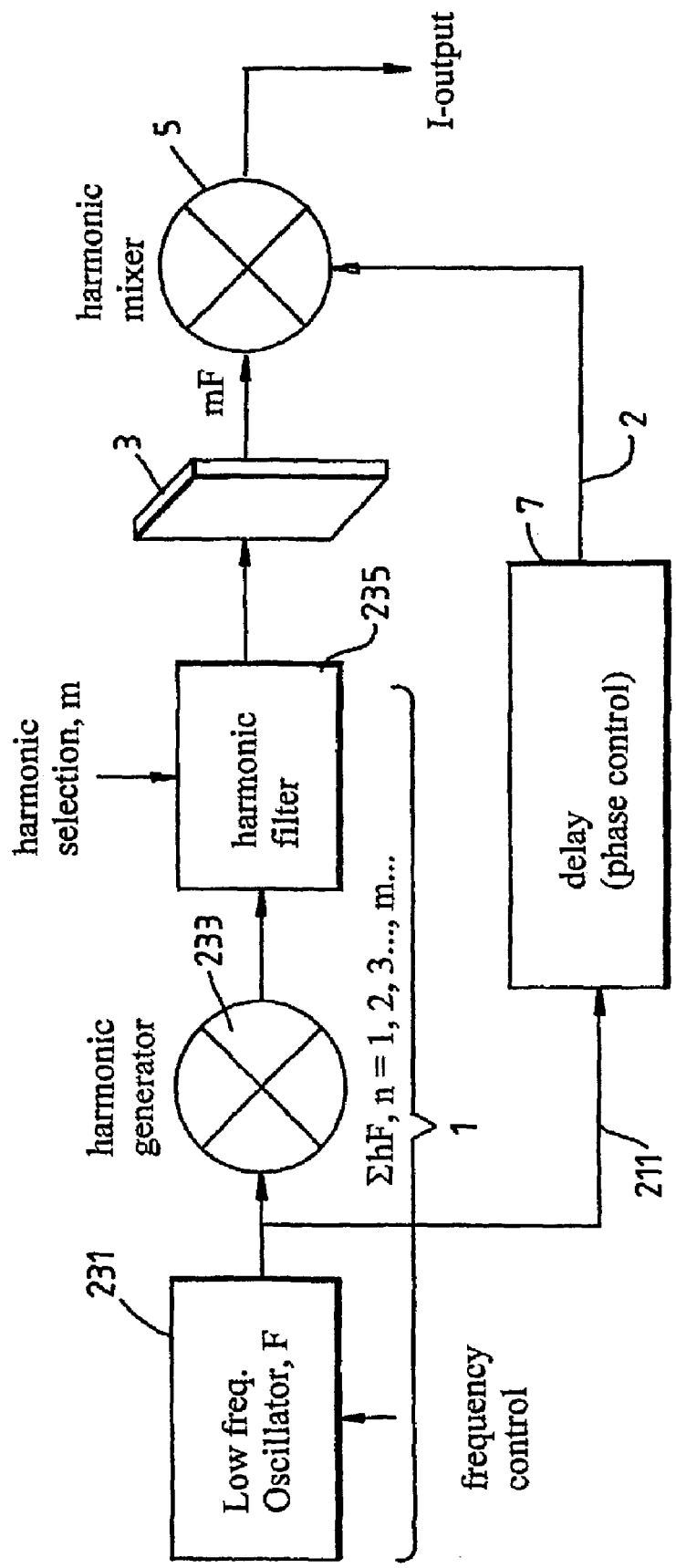
FIG. 17 shows an imaging system in accordance with an embodiment of the present invention using a frequency multiplier.

FIG. 17 shows a further variation on the imaging system of FIGS. 1 and 2. This system follows the same basic design system of FIGS. 1 and 2. The source is a harmonic source which emits radiation with frequency below that of the THz range. The emitted frequency is such that doubling or tripling etc of the frequency will give radiation with a frequency in that of the THz regime. The radiation emitted from low frequency oscillator is divided. One signal is fed into optical delay line 211 (as described with reference to FIG. 12), the other signal is fed into harmonic generator 233, which generates a plurality of harmonics for the frequency. The harmonic generator may be a Schottky diode or an optically non-linear crystal. The radiation emitted by harmonic generator 233 is then fed into harmonic filter 235 which selects the desired harmonic in the THz range. The radiation is then directed onto sample 3. The sample can be rastered with respect to the beam of incident radiation or the beam can be moved with respect to the sample. Once the radiation has been transmitted through the sample 3, it is directed into harmonic detector 5 where it is recombined with the probe beam 209. The harmonic mixer can be a Schottky diode which will output a signal corresponding to the strength of the detected THz field.

Figure 18:
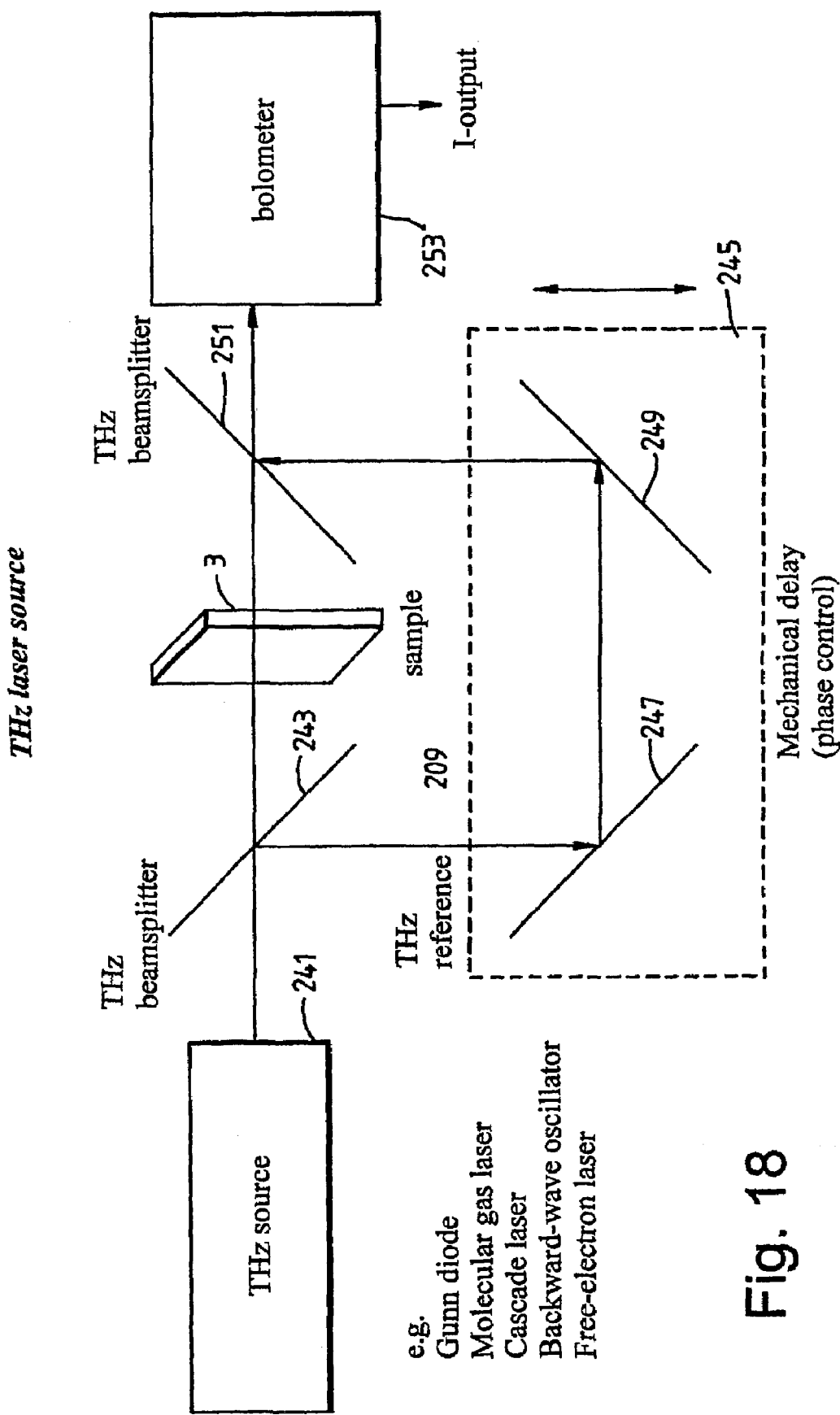
FIG. 18 shows an imaging system in accordance with an embodiment of the present invention, using a laser source which can directly output radiation in the desired frequency range.

FIG. 18 shows a further variation on the imaging systems of FIGS. 1 and 2. Here, the THz can be generated by using THz source which does not used the method of converting the frequency of an input beam, instead, the source directly outputs THz radiation in response to an input parameter such as a bias applied across the source. Typical sources are Gunn diodes, Molecular gas lasers, cascade lasers, backward wave oscillators and free electron lasers. A beam of THz radiation is outputted from this direct THz source 241 onto THz beam splitter 243 which splits the beam into probe beam 209 which is fed into optical delay line 245 and the imaging radiation is directed onto the sample 3. Optical delay line 245 comprise two mirrors 247 and 249, the probe beam 209 is directed onto mirror 247 and then onto mirror 249. The separation between the two mirrors can be varied so that the path length of the probe beam can be varied as required.

The probe beam 209 is then combined with the radiation which is transmitted through sample 3 using beam combiner 251. The output of beam combiner 251 is then fed into bolometer 253 which outputs a current which is related to the detected THz field.

Figure 19:
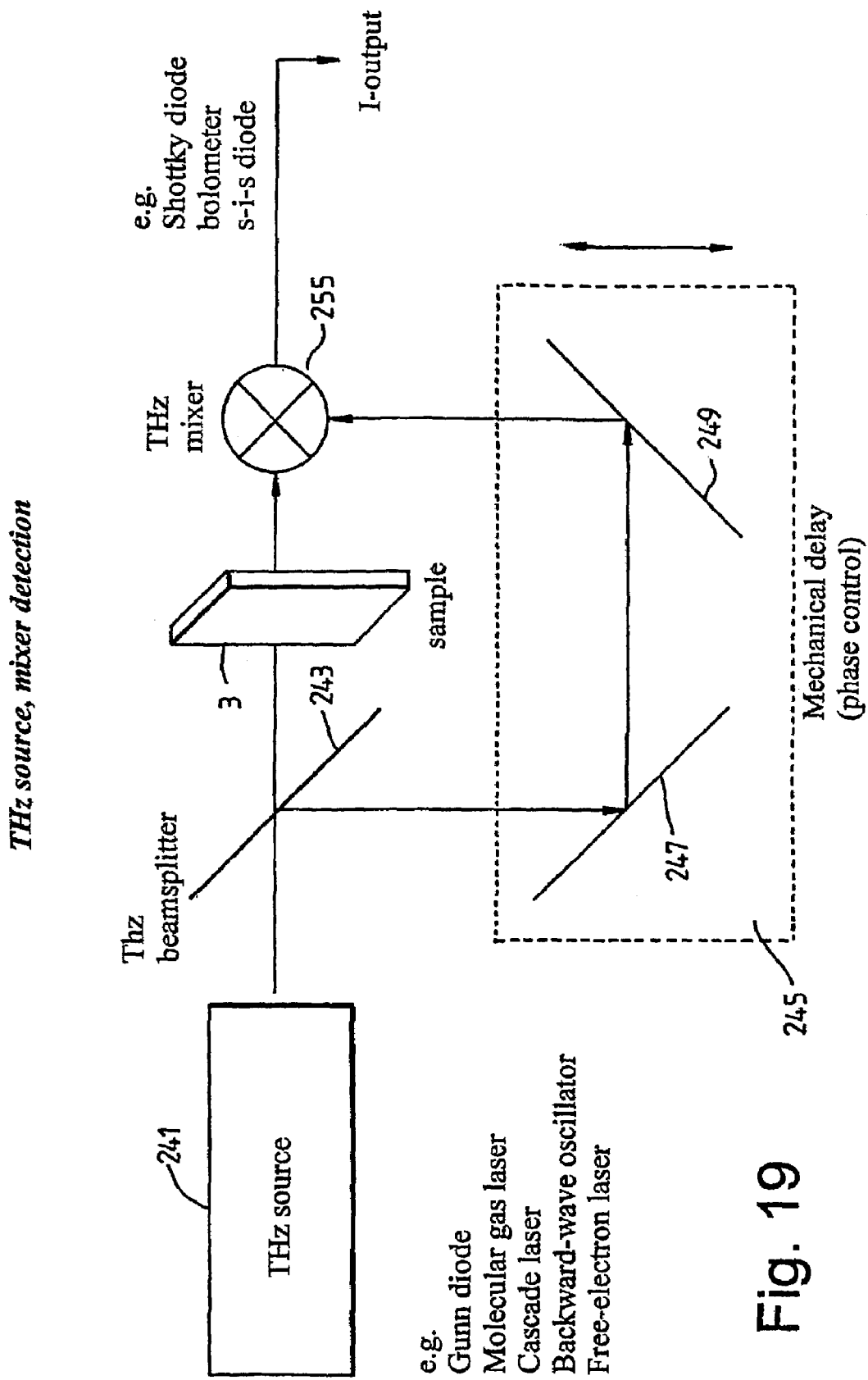
FIG. 19 shows a variation of the imaging system of FIG. 18 using an optical mixer.

FIG. 19 shows a variation on the imaging system of FIG. 18. Here, the beam combiner 251 is replaced with a THz mixer 255 which can be a Schottky diode, bolometer, semiconductor-insulator-semiconductor diode and outputs a current which is related to the strength of the detected THz field.

Figure 20:
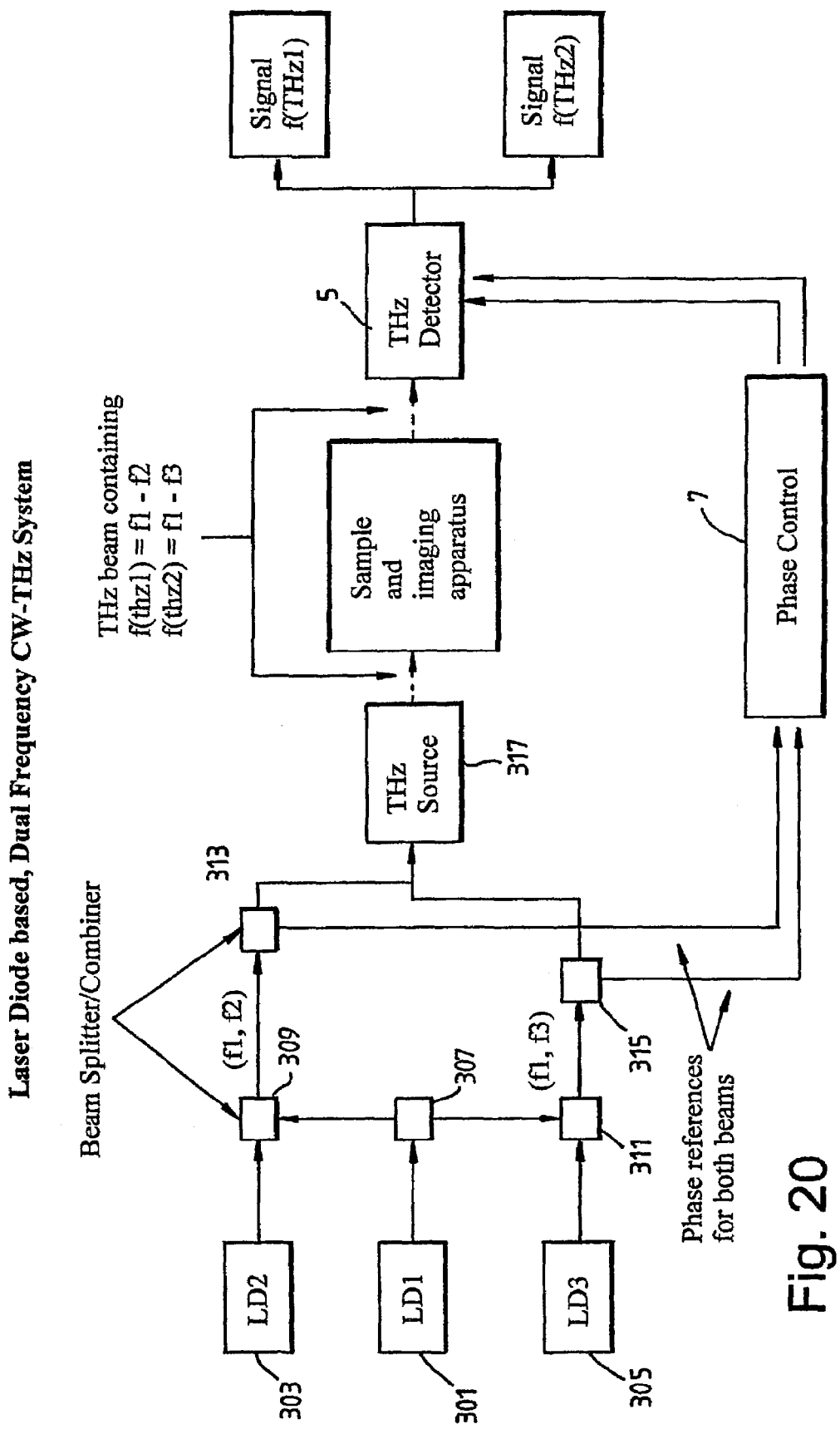
FIG. 20 shows a dual frequency imaging system in accordance with an embodiment of the present invention.

FIG. 20 shows a further possible variation on the imaging systems of FIGS. 1 and 2. Here, the sample is illuminated with two frequencies in the THz range. The THz generator is based on the generator described with reference to FIGS. 3 and 4. There are three laser diodes, 301, 303 and 305. The first laser diode 301 emits radiation with a frequency $\omega_1$ into beam splitter 307. Beam splitter 307 directs part of the beam into beam combiner 309 where it combines with radiation of a frequency $\omega_2$ emitted from the second diode. The other part of the beam is directed towards combiner 311, where it is combined in beam combiner 311 with radiation from the third diode 305 having a frequency $\omega_3$.

Radiation from beam combiner 309 is directed into beam splitter 313 which in turn splits the beam into an input for the phase control means 7 and an input for the THz source 317.

Radiation from beam combiner 311 is directed into beam splitter 315 where it is split into an input for the phase control means 7 and an input to the THz source 317. The THz source is configured to output beams in the THz range with frequencies $\omega_1-\omega_2$ and $\omega_1-\omega_3$. These two beams travel through the sample 3. Typically, the two THz frequencies $\omega_1-\omega_2$ and $\omega_1-\omega_3$ will be chosen such that they can be used to probe different materials which make up the sample 3.

The two transmitted THz beams are combined with the two reference beams as previously described. The detector can be any type of detector which has been previously described for the use of one THz beam. The different frequency components can be split by Fourier transforming the signal obtained due to the detected radiation.

One major disadvantage with the use of pulsed radiation is that it is very difficult to transmit the pulses along waveguides/optical fibres and the like due to substantial losses. The use of CW radiation overcomes this problem. Hence, it is possible to make a small probe which can be used to detect the response of a system to THz radiation as a large part of the THz generator and the detector can be located remote from the probe.

Figure 21:
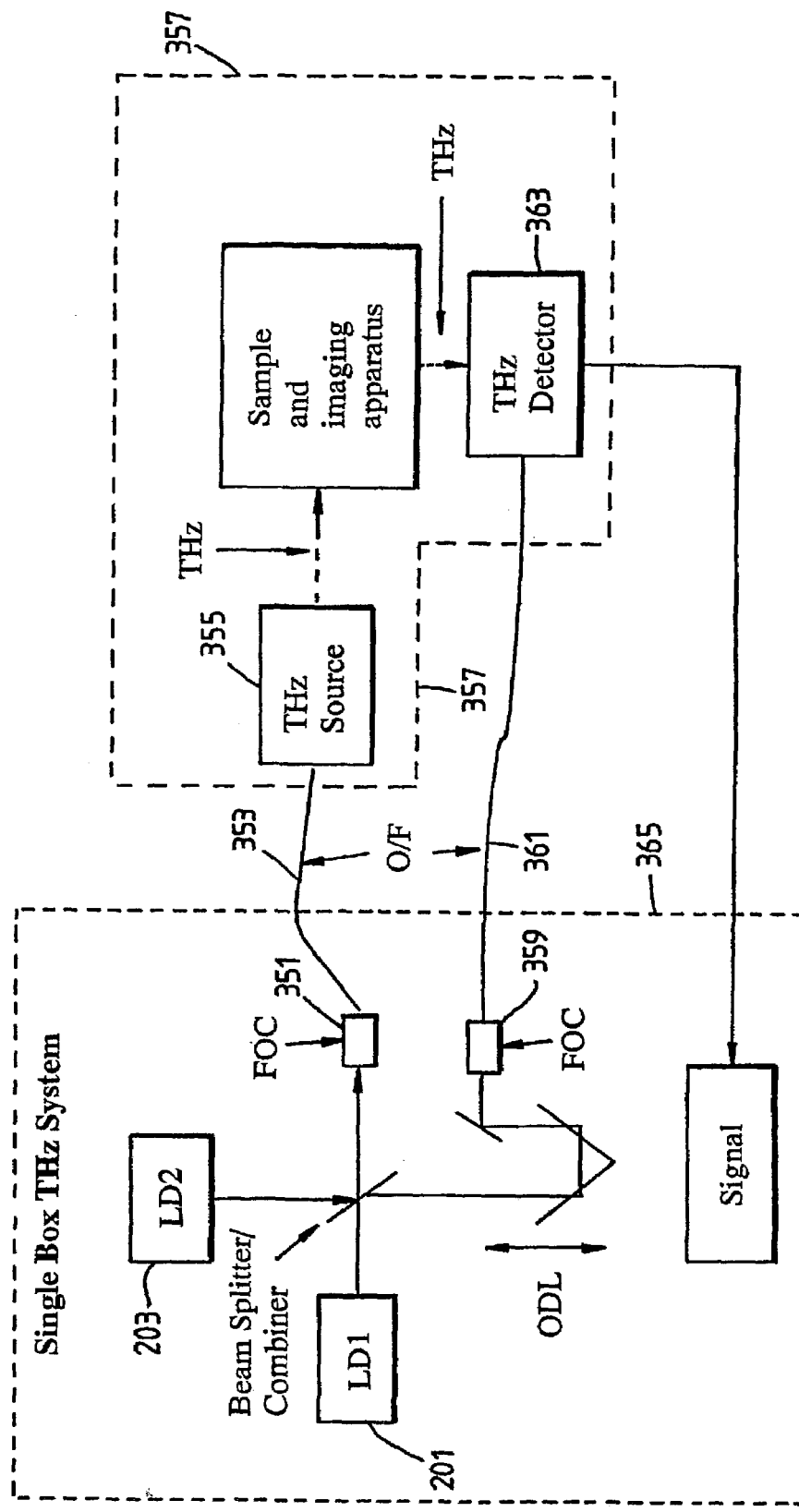
FIG. 21 shows an imaging probe in accordance with an embodiment of the present invention.

FIG. 21 shows such a system. The imaging system is largely based on the system of FIG. 12. Therefore to avoid unnecessary repetition like numerals will be used to denote like features. As in FIG. 12, radiation from laser diodes 201 and 203 are combined using beam splitter/coupler 205. Part of this combined radiation is sent to fibre optic coupler 351 which directs the radiation into fibre optic cable 353 which carries the radiation to THz source 355 which generates the THz radiation to irradiate sample 3. THz source and imaging optics 3 are remote from the laser diodes 201, 203 in probe head 357.

The other part of the beam from beam/splitter combiner 205 is directed into optical delay line 211 which is the same as that described with reference to FIG. 12. However, mirror 215 directs the probe beam 209 into fibre optic coupler 359 which in turn direct the radiation into fibre optic cable 361 where it is carried towards THz detector part 363. Terahertz detector part 363 combines the radiation transmitted through sample 3 with that of the probe beam. It serves to convert the THz radiation into some form which it can be transmitter back to the system box 365 for analysis.

Figure 22:
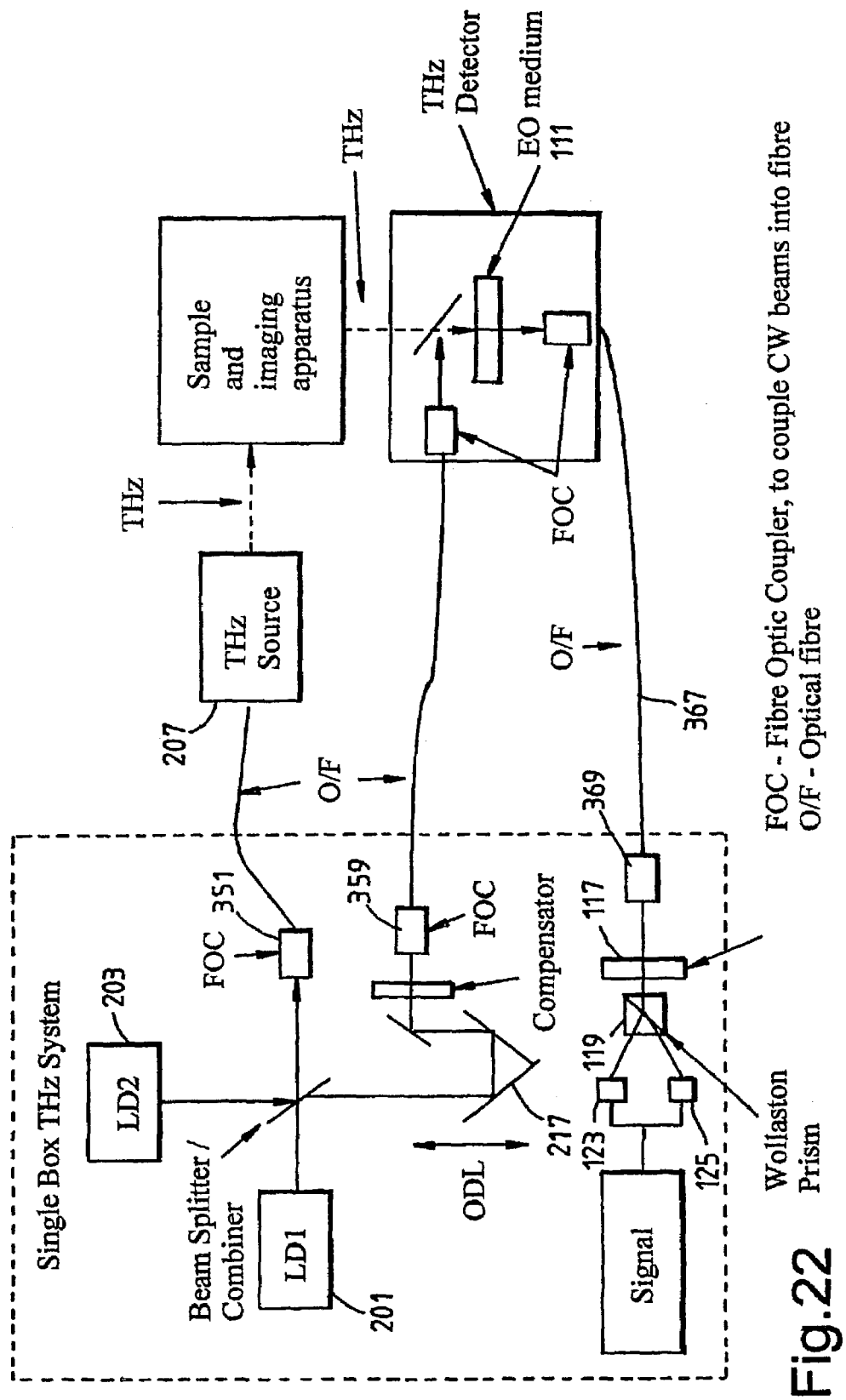
FIG. 22 shows a further detail of the imaging system of FIG. 21.

FIG. 22 shows an imaging system similar to that of FIG. 21, but having an EOS based detection system, of the type described with reference to FIG. 3. Here, the detection member 111 is housed remote from the box system. The probe beam with the rotated polarisation is then fed back to the signal box using polarization preserving fibre 367. The radiation leaves fibre 367 and is directed onto quarter waveplate using fibre optic coupler 369. The remainder of the detection is then the same as described with relation to FIG. 13 and will not be repeated here.

Figure 23:
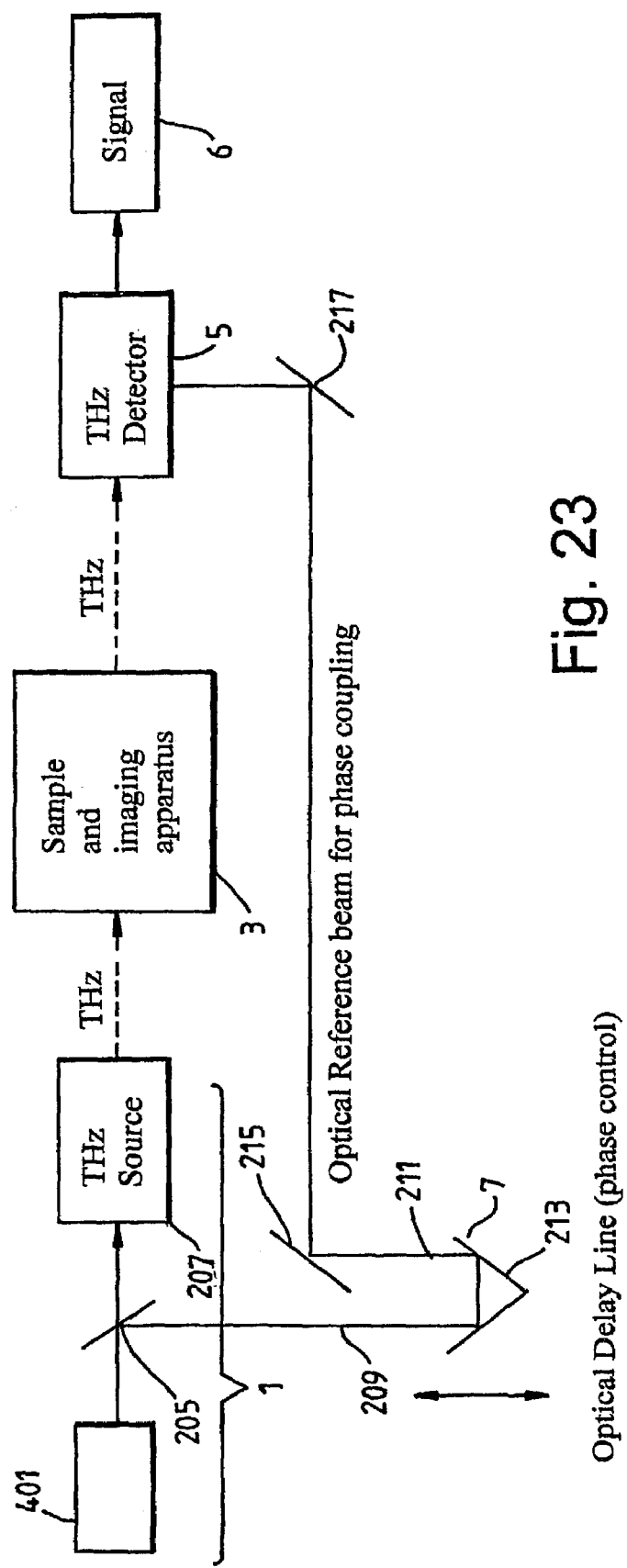
FIG. 23 shows an apparatus in accordance with an embodiment of the present invention using a broadband source.

FIG. 23 shows a system which can be used for imaging or investigating a sample using THz radiation. The system is similar to that described with reference to FIG. 12. Therefore, to avoid unnecessarily repetition, like reference numerals will be used to denote like features.

The imaging system of FIG. 12 used two laser diodes 201, 203 which are configured to emit radiation with the frequencies of $\omega_1$ and $\omega_2$. The apparatus of FIG. 23 uses a single broadband source 401 to generate radiation which is directed into THz source 207. THz source 207 is a difference frequency source which can use the difference frequency generation methods described with reference to FIGS. 3 to 5.

The broadband laser 401 emits radiation having a plurality of frequencies. THz source 207 then emits THz radiation having a plurality of frequencies, each of the plurality of frequencies corresponding to a difference between two of the frequencies from the broadband source 401.

Examples of widely available broadband sources are "superluminence LEDs" or amplified spontaneous emission light sources based on Er-doped fibre amplifiers. Both of these types of sources generate broadband, low-coherence light centred around 1550 nm wavelengths. Typical bandwidths are from 20 to 50 nm corresponding to 2 to 5 THz.

Specifically "Newport" sell one such system under their part number PTS-BBS, as do "ILX Lightwave" under their part number MPS-8033APE. Another example of a source is E-tek who sell a broadband source working at 980 nm, part number BLS980.

In the same manner as described with reference to FIG. 12, the beam from the broadband source 401 is divided using beamsplitter 205 which generates a reference beam which is supplied to the THz detector 5. The broadband wave source only has a short-coherent length and can be essentially thought of as being incoherent. There is no definite phase relationship between the frequencies i.e. the laser modes are all independent of each other. Thus, there is a random phase at each frequency. However, as part of the broadband laser source beam is used as the probe beam, the random phase relationship between different frequencies does not matter because the detection method only measures the phase difference between the THz pump and probe beam. Thus, it is possible to determine the actual phase change for each frequency component.

As the above apparatus illustrates a system where THz power is delivered in a continuous manner as opposed to a pulsed manner, this system is also advantageous for delivering radiation down optical fibres. Therefore, this type of broadband source can be used in the fibre delivery system detailed in FIGS. 21 and 22.

The above system can be used for imaging or it can be used to obtain information about a sample at a point.

Any of the previously described detection mechanisms can be used with the broadband source 401 described with reference to FIG. 23.

The invention claimed is:

1. An apparatus for imaging a sample, the apparatus comprising:
   a source for irradiating a sample with a beam of substantially continuous electromagnetic radiation having a frequency in the range 25 GHz to 100 THz;
   means for subdividing an area of the sample which is to be imaged into a two dimensional array of pixels,
   a detector for detecting radiation from each pixel wherein the detector is configured to detect a phase dependent quantity of the detected radiation which is measured relative to the radiation which irradiates the sample, and a probe beam having a phase related to that of the radiation leaving the source is provided for detection by the detector.

2. An apparatus according to claim 1, wherein the source emits radiation having at least one frequency component and said detector is configured to detect a phase dependent quantity of each frequency component of the detected radiation relative to the radiation which irradiates the sample.

3. An apparatus according to claim 1, wherein the source emits coherent radiation.

4. An apparatus according to claim 1, wherein the apparatus further comprise phase control means in order for the detector to determine a phase dependent quantity of the radiation.

5. An apparatus according to claim 4, wherein phase control means comprises means for varying the optical path of the probe beam between the source and the detector.

6. An apparatus according to claim 5, wherein the path length of the probe beam can oscillate about a length in order to allow the detector to lock-in to the oscillation frequency of the path length.

7. An apparatus according to claim 1, wherein the probe beam is obtained by dividing the beam of radiation which is used to irradiate the sample.

8. An apparatus according to claim 1, wherein the source comprises a frequency conversion member which is configured to emit a beam of emitted radiation in response to being irradiated by at least one beam of input radiation, wherein the emitted radiation has a different frequency to that of the input radiation.

9. An apparatus according to claim 1, wherein the source comprises a frequency conversion member which is configured to emit a beam of emitted radiation in response to being irradiated by at least one beam of input radiation, and wherein the emitted radiation has a different frequency to that of the input radiation at least one input beam is divided in or order to provide the probe beam.

10. An apparatus according to claim 1, wherein the source is a broadband incoherent source or short coherent length source.

11. An apparatus according to claim 1, wherein the radiation which is transmitted through or reflected from the sample is combined with a probe beam prior to entering the detector.

12. An apparatus according to claim 1, wherein the probe beam has a frequency substantially equal to that of the radiation which irradiates the sample.

13. An apparatus according to claim 1, wherein the source radiation with a single frequency component.

14. An apparatus according to claim 1, wherein the source emits radiation at least two distinguishable frequency components.

15. An apparatus according to claim 1, wherein said information about the structure of the sample is information about the thickness of the sample, or information about the refractive index of at least part of the sample.

16. A method of imaging a sample, the method comprising the steps of:
   irradiating a sample with substantially continuous radiation with a frequency in the range form 25 GHz to 100 THz;
   subdividing an area of the sample which is to be imaged into a two dimensional array of pixels
   detecting radiation from each pixel, wherein the detector is configured to detect a phase dependent quantity of the detected radiation which is measured relative to the radiation which irradiates the sample, and wherein a probe beam having a phase related to that of the radiation leaving the source is provided for detection by the detector.

17. An apparatus for investigating a sample, the apparatus comprising:
   means for generating a beam of substantially continuous electromagnetic source radiation having a frequency in the range 25 GHz to 100 THz;
   means for moving the sample relative to the beam to scan the beam over the sample;
   means for detecting the radiation transmitted by or reflected from the sample;
   wherein the means for detecting includes means for detecting a change in a phase dependent quantity of the transmitted or reflected radiation relative to the source, and wherein a probe beam having a phase related to that of the radiation leaving the source is provided for detection by the detector.

18. An apparatus according to claim 17, wherein the source radiation comprises at least one frequency component and said means for detecting is configured to detect a change in a phase dependent quantity of each frequency component of the transmitted or reflected radiation.

19. An apparatus according to claims 17 further comprising means to generate an image of the object.

20. An apparatus according to claim 19, including means for providing an image of the object based on the output of the detecting means and showing the variation of the absorption or transmission characteristic of the object, the refractive index and/or the thickness.

21. An apparatus for investigating a sample, the apparatus comprising:
- means for generating a beam of substantially continuous electromagnetic source radiation having a frequency in the range 25 GHz to 100 THz;
- means for moving the sample relative to the beam to scan the beam over the sample;
- means for detecting the radiation transmitted by or reflected from the sample;
- wherein the means for detecting includes means for comparing a phase dependent quantity of the transmitted or reflected radiation with that of the source radiation, and wherein probe beam having a phase related to that of the radiation leaving the source is provided for detection by the detector.

22. An apparatus according to claim 21, wherein source radiation comprises at least one frequency component and said means for detecting is configured to compare a phase dependent quantity of the transmitted or reflected radiator with the source radiation for each frequency component.

23. An apparatus for investigating a sample, the apparatus comprising:
- means for generating a beam of substantially continuous electromagnetic source radiation having at least two frequency components in the range from 25 GHz to 100 THz;
- means for detecting radiation transmitted by or reflected from the sample;
- wherein the means for detecting includes means for detecting a change in a phase dependent quantity of each frequency component of the transmitted or reflected radiation relative to the source radiation, and wherein a probe beam having a phase related to that of the radiation leaving the source is provided for detection by the detector.

24. An apparatus for investigating a sample, the apparatus comprising:
- means for generating a beam of substantially continuous electromagnetic source radiation having at least two frequency components in the range from 25 GHz to 100 THz;
- means for detecting radiation transmitted by or reflected from the sample;
- wherein the means for detecting includes means for comparing a phase dependent quantity of each frequency component of the transmitted or reflected radiation with that of the source radiation, and wherein a probe beam having a phase related to that of the radiation leaving the source is provided for detection by the detector.

* * * * *